United States Patent
Meulewaeter et al.

(10) Patent No.: US 9,163,252 B2
(45) Date of Patent: Oct. 20, 2015

(54) FIBER-PREFERENTIAL PROMOTER IN COTTON

(71) Applicants: Bayer CropScience NV, Diegem (BE); Commonwealth Scientific and Industrial Research Organisation, Campbell (AU)

(72) Inventors: Frank Meulewaeter, Merelbeke (BE); Danny J. Llewellyn, O'Connor (AU)

(73) Assignees: Bayer CropScience NV, Diegem (BE); Commonwealth Scientific and Industrial Research Organisation, Campbell (AU)

( * ) Notice: Subject to any disclaimer, the term of this patent is extended or adjusted under 35 U.S.C. 154(b) by 312 days.

(21) Appl. No.: 13/630,119

(22) Filed: Sep. 28, 2012

(65) Prior Publication Data

US 2013/0081154 A1   Mar. 28, 2013

Related U.S. Application Data

(60) Provisional application No. 61/540,055, filed on Sep. 28, 2011.

(51) Int. Cl.
*C12N 15/82* (2006.01)
*C12N 15/00* (2006.01)
*C07K 14/415* (2006.01)

(52) U.S. Cl.
CPC .......... *C12N 15/8233* (2013.01); *C07K 14/415* (2013.01); *C12N 15/8222* (2013.01); *C12N 15/8223* (2013.01); *C12N 15/8237* (2013.01); *C12N 15/8241* (2013.01); *C12N 15/8242* (2013.01); *C12N 15/8261* (2013.01)

(58) Field of Classification Search
None
See application file for complete search history.

(56) References Cited

U.S. PATENT DOCUMENTS

2003/0106089 A1* 6/2003 McBride et al. .............. 800/278

OTHER PUBLICATIONS

Potenza_In Vitro Cell Dev Biol Plant_40_1_2004.*
Dolferus_Plant Phys_105_1075_1994.*
Donald_EMBO J_9_1717_1990.*
Kim_Plant Mol Biol_24_105_1994.*
Fourgoux-Nicol Plant Mol Biol 40 857 1999.*
Jagtap_Naturwissenschaften_98_473_2011.*
Wahl-Meth Enzymol—152-399-1987.*
Schwab_Plant Cell_18_1121_2006.*

* cited by examiner

*Primary Examiner* — Medina A Ibrahim
*Assistant Examiner* — Russell Boggs

(57) ABSTRACT

The present application discloses a chimeric gene comprising a promoter region consisting of the nucleotide sequence of SEQ ID NO: 1 from nucleotide 1 to nucleotide 1437 operably linked to a nucleic acid coding for an expression product of interest, and a transcription termination and polyadenylation sequence. Also disclosed herein are a vector, a transgenic plant cell, a transgenic plant and a seed comprising such a chimeric gene. Methods disclosed herein relate to the production of a transgenic plant, growing cotton, producing a seed, effecting fiber-preferential expression of a product in cotton and of altering fiber properties in a cotton plant using the chimeric gene described.

19 Claims, 12 Drawing Sheets

Figure 2

Figure 1:
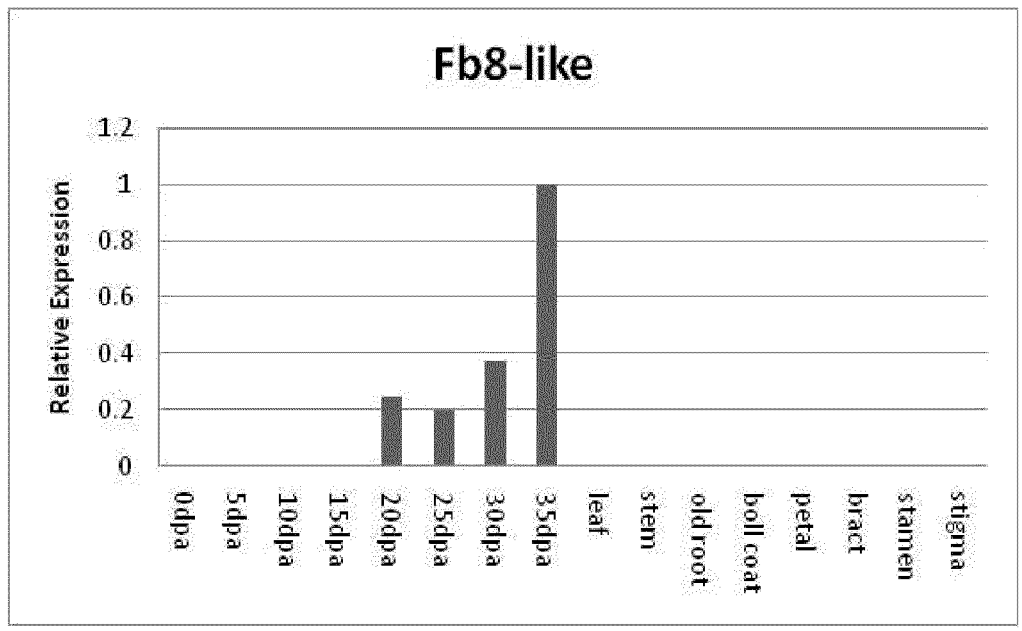

```
      150F2  MAHSIRHPFFLFQLLLISVSLVTGSHTVSAAARRLFETQA   40
  cFB8-like#1 MAHNFRHPFFLFQLLLITVSLMIGSHTVSSAARHLFHTQT   40

150F2  TSSELPQLASKYEKHEESEYEKPEYKQPKYHEEYSKLEKP   80
  cFB8-like#1 TSSELPQLASKYEKHEES-----EYKQPKYHEEYPKHEKP   75

150F2  EMQKEEKQKPCKQHEEYHESHESKEQKEYEKENLEFPKWE  120
  cFB8-like#1 EMYKEEKQKPCKHHEEYHESRESKEHEEYDKEKPDFPKWE  115

150F2  KPKEHEKHEVEYPKIPEYKVKQDEGKEHKHEEYHESRESK  160
  cFB8-like#1 KPKEHEKHEVEYPKIPEYKDKQDEDKEHKNEEYHESRESK  155

150F2  EHEEYEKEKPEFPKLEKPKEHEKHEVEYPEIPEYKKKQDE  200
  cFB8-like#1 EHEEYEKEKPEFPKREKPKEHEKHEVEYSEIPEYKEREDK  195

150F2  GNEHK-------HEFPKHEKEEEKKP-----EK-------  221
  cFB8-like#1 SKKHKDEECQESHESKEHEEYEKEKPDFPKWEKPKGHEKH  235

150F2  KAEY---------LEWAK-----MPEWSKSMFTQPGSATK  247
  cFB8-like#1 KAEYPKIPECKEKLDEDKEHKHEFPKHEKEEEKKPEKGIV  275

150F2  P                                         248
  cFB8-like#1 P                                         276
```

A

Figure 4B

```
TTGTACAAAGTGGTCTCGATCGAGGAATTCGATTCGACCATGGTCCGTCCTGTAGAAACCCCAACCC
GTGAAATCAAAAAACTCGACGGCCTGTGGGCATTCAGTCTGGATCGCGAAAACTGTGGAATTGATCA
GCGTTGGTGGGAAAGCGCGTTACAAGAAAGCCGGGCAATTGCTGTGCCAGGCAGTTTTAACGATCAG
TTCGCCGATGCAGATATTCGTAATTATGCGGGCAACGTCTGGTATCAGCGCGAAGTCTTTATACCGA
AAGGTTGGGCAGGCCAGCGTATCGTGCTGCGTTTCGATGCGGTCACTCATTACGGCAAAGTGTGGGT
CAATAATCAGGAAGTGATGGAGCATCAGGGCGGCTATACGCCATTTGAAGCCGATGTCACGCCGTAT
GTTATTGCCGGGAAAAGTGTACGTATCACCGTTTGTGTGAACAACGAACTGAACTGGCAGACTATCC
CGCCGGGAATGGTGATTACCGACGAAAACGGCAAGAAAAAGCAGTCTTACTTCCATGATTTCTTTAA
CTATGCCGGAATCCATCGCAGCGTAATGCTCTACACCACGCCGAACACCTGGGTGGACGATATCACC
GTGGTGACGCATGTCGCGCAAGACTGTAACCACGCGTCTGTTGACTGGCAGGTGGTGGCCAATGGTG
ATGTCAGCGTTGAACTGCGTGATGCGGATCAACAGGTGGTTGCAACTGGACAAGGCACTAGCGGGAC
TTTGCAAGTGGTGAATCCGCACCTCTGGCAACCGGGTGAAGGTTATCTCTATGAACTGTGCGTCACA
GCCAAAAGCCAGACAGAGTGTGATATCTACCCGCTTCGCGTCGGCATCCGGTCAGTGGCAGTGAAGG
GCGAACAGTTCCTGATTAACCACAAACCGTTCTACTTTACTGGCTTTGGTCGTCATGAAGATGCGGA
CTTACGTGGCAAAGGATTCGATAACGTGCTGATGGTGCACGACCACGCATTAATGGACTGGATTGGG
GCCAACTCCTACCGTACCTCGCATTACCCTTACGCTGAAGAGATGCTCGACTGGGCAGATGAACATG
GCATCGTGGTGATTGATGAAACTGCTGCTGTCGGCTTTAACCTCTCTTTAGGCATTGGTTTCGAAGC
GGGCAACAAGCCGAAAGAACTGTACAGCGAAGAGGCAGTCAACGGGGAAACTCAGCAAGCGCACTTA
CAGGCGATTAAAGAGCTGATAGCGCGTGACAAAAACCACCCAAGCGTGGTGATGTGGAGTATTGCCA
ACGAACCGGATACCCGTCCGCAAGTGCACGGGAATATTTCGCCACTGGCGGAAGCAACGCGTAAACT
CGACCCGACGCGTCCGATCACCTGCGTCAATGTAATGTTCTGCGACGCTCACACCGATACCATCAGC
GATCTCTTTGATGTGCTGTGCCTGAACCGTTATTACGGATGGTATGTCCAAAGCGGCGATTTGGAAA
CGGCAGAGAAGGTACTGGAAAAAGAACTTCTGGCCTGGCAGGAGAAACTGCATCAGCCGATTATCAT
CACCGAATACGGCGTGGATACGTTAGCCGGGCTGCACTCAATGTACACCGACATGTGGAGTGAAGAG
TATCAGTGTGCATGGCTGGATATGTATCACCGCGTCTTTGATCGCGTCAGCGCCGTCGTCGGTGAAC
AGGTATGGAATTTCGCCGATTTTGCGACCTCGCAAGGCATATTGCGCGTTGGCGGTAACAAGAAAGG
GATCTTCACTCGCGACCGCAAACCGAAGTCGGCGGCTTTTCTGCTGCAAAAACGCTGGACTGGCATG
AACTTCGGTGAAAAACCGCAGCAGGGAGGCAAACAATGAATCAACAACTCTCCTGGCGCACCATCGT
CGGCTACAGCCTCGGGAATTCCTGCAGCCCGGGGGATCCGCTAGCG
```

Figure 4B contd.

```
TTTAGCGGGGGAAAAAGGACAGTTGATCTGTTGCTGTTTGCAATTTTTTAAAGGGTATGTTGTCAGA
TGCATGTTGTAATGCTTGTTCATCAACACATTATATGACTTGCAGTTGCTGATGATGGAAACTTAAA
GCTTAATACTACTTTTGTTTATTCACTTACAAATACCGGTTGGGTTCTTTGTTTATCAGGAATGCTC
ATTGTATGTAGCTAAAAGCTGGCCGTTTATAGTTTTATTGCCCTAAATCTGGTACTTTATCCAAAAA
CTAAATTTGGAAACATCAAATACTTTTTTCAAGAATGATAAACTCGTACACTCTCTAGGGTACTCCT
GAAATTTAAATCAAAATCCAAAACCGCTTAGGAAGGAACATATGTGATAAGAACTGAAATTTCGATT
AACTATTACAAGATAGTCGGCCCAATTCGAGAGGACTAGTCTCCGATTACAAGGAGTAAATATCTTA
ATCTTGATAAACAAAACACATATAAAAAACCTAAAAATATAGGAACATAATACATAAACTAAAAGTT
GTGGGAACAGTTACAAATCTGCAGTCTCACTCCCTAAATTTGTGAGTCACCTTTCACCTCCAAGTTT
TCGAATGTTCTCCCACCATTCACTTTCCCTCCACCCGGATTCCCTCCAATTAATAGCTGACACAACC
CGTTTTGACCCAACATTGGGTTCGTATCAATACATCCGGCCCGGAAAATCGACTTGTCCTCAAGTCG
AAAGGAGGGGAATTATTGTGCCAAGCAAAAAGCCATTCGATTGGAGGTTGATGGATGATTTCCTTGT
GTTTGAAAGCTTCAAAAGATCCGGCCAAATCAGCTTTTAATGCCTCTTGAACTGTAGCCACAACACC
ACTTTGAAACCTCAAATCTGTTTTCAATTGGGATCCACTAGTTCTAGAGCGGCCGCTCTAGTCGAGT
CTAGAAAGCTTCCAACAAAAACATAACACACCGCTTCGCGGAGTAATTCAAAGA
ATAATAACAACTCTTTATTCATTAATCACAATTACATCTCATAATTCTATCTTAATAGAACCTCTAT
CAATTACAATAGACATAAACTCAATACCGTCGACCCGGGGTGGGCGAAGAACTCCAGCATGAGATCC
CCGCGCTGGAGGATCATCCAGCCGGCGTCCCGGAAAACGATTCCGAAGCCCAACCTTTCATAGAAGG
CGGCGGTGGAATCGAAATCTCGTGATGGCAGGTTGGGCGTCGCTTGGTCGGTCATTTCGAACCCCAG
AGTCCCGCTCAGAAGAACTCGTCAAGAAGGCGATAGAAGGCGATGCGCTGCGAATCGGGAGCGGCGA
TACCGTAAAGCACGAGGAAGCGGTCAGCCCATTCGCCGCCAAGCTCTTCAGCAATATCACGGGTAGC
CAACGCTATGTCCTGATAGCGGTCCGCCACACCCAGCCGGCCACAGTCGATGAATCCAGAAAAGCGG
CCATTTTCCACCATGATATTCGGCAAGCAGGCATCGCCATGGGTCACGACGAGATCCTCGCCGTCGG
GCATGCGCGCCTTGAGCCTGGCGAACAGTTCGGCTGGCGCGAGCCCCTGATGCTCTTCGTCCAGATC
ATCCTGATCGACAAGACCGGCTTCCATCCGAGTACGTGCTCGCTCGATGCGATGTTTCGCTTGGTGG
TCGAATGGGCAGGTAGCCGGATCAAGCGTATGCAGCCGCCGCATTGCATCAGCCATGATGGATACTT
TCTCGGCAGGAGCAAGGTGAGATGACAGGAGATCCTGCCCCGGCACTTCGCCCAATAGCAGCCAGTC
CCTTCCCGCTTCAGTGACAACGTCGAGCACAGCTGCGCAAGGAACGCCCGTCGTGGCCAGCCACGAT
AGCCGCGCTGCCTCGTCCTGCAGTTATCATCATCATCATAGACACACGAAATAAAGTAA
```

Figure 4B contd.

```
TCAGATTATCAGTTAAAGCTATGTAATATTTACACCATAACCAATCAATTAAAAAATAGATCAGTTT
AAAGAAAGATCAAAGCTCAAAAAAATAAAAAGAGAAAAGGGTCCTAACCAAGAAAATGAAGGAGAAA
AACTAGAAATTTACCTGCAGTTCATTCAGGGCACCGGACAGGTCGGTCTTGACAAAAAGAACCGGGC
GCCCCTGCGCTGACAGCCGGAACACGGCGGCATCAGAGCAGCCGATTGTCTGTTGTGCCCAGTCATA
GCCGAATAGCCTCTCCACCCAAGCGGCCGGAGAACCTGCGTGCAATCCATCTTGTTCAATCATTGTT
ATCGGCGCTATGAAATTCTGAACAATCTGTTCAGAAGCACTCTATTTATAGACCCAAGACAACGCGT
ACTAAGTACGCTAACTAGATCTAAGTGTGAACGCTCTTCCGTCAGATTCGTTCAGCTTAAGCGCTTC
ACTAGCATCACAGATCCTGAGCGTCCACGTGTCATTTAATCCAAGGGCTATTATACTAGTCAACTAT
TGGTCAAATGTCTCTGATCCCGGCACGGGGGTAATACTAAGCCCCGTGCTGACGTAGGCACGGAGAC
ATATGACGTCATCAAAACGCTTCGTTTCATTTATCACTTAACATATCGCTTCGCGGAATTAAATTAA
AACAATAATAATATATCTATTATCTTATTTCAGCCACTCACAACTTGACACGTTTACAGCCGCAATT
TCACTAACGCGCCAAAACCAAATTCAAATTAAAGTTATACGCTGCTTCGAGGAAGCTAGCTTAAAAA
ACACAGACGAAGAACAGAATAATAATAATTCTCATTAATCCATATAAAATTACAACATAGGATCCTC
TAGAGCGGCCCTAGAATTAATTCAGTACATTAAAAACGTCCGCAATGTGTTATTAAGTTGTCTAAGC
GTCAATTTGTTTACACCACAATATATCCTGCCACCAGCCAGCCAACAGCTCCCCGACCGGCAGCTCG
GCACAAAATCACCACTCGATACAGGCAGCCCATCAGTCCGGGACGGCGTCAGCGGGAGAGCCGTTGT
AAGGCGGCAGACTTTGCTCATGTTACCGATGCTATTCGGAAGAACGGCAACTAAGCTGCCGGGTTTG
AAACACGGATGATCTCGCGGAGGGTAGCATGTTGATTGTAACGATGACAGAGCGTTGCTGCCTGTGA
TCAAATATCATCTCCCTCGCAGAGATCCGAATTATCAGCCTTCTTATTCATTTCTCGCTTAACCGTG
ACAGGCTGTCGATCTTGAGAACTATGCCGACATAATAGGAAATCGCTGGATAAAGCCGCTGAGGAAG
CTGAGTGGCGCTATTTCTTTAGAAGTGAACGTTGACGATCGTCGACGGATCTTTTCCGCTGCATAAC
CCTGCTTCGGGGTCATTATAGCGATTTTTTCGGTATATCCATCCTTTTTCGCACGATATACAGGATT
TTGCCAAAGGGTTCGTGTAGACTTTCCTTGGTGTATCCAACGGCGTCAGCCGGGCAGGATAGGTGAA
GTAGGCCCACCCGCGAGCGGGTGTTCCTTCTTCACTGTCCCTTATTCGCACCTGGCGGTGCTCAACG
GGAATCCTGCTCTGCGAGGCTGGCCGGCTACCGCCGGCGTAACAGATGAGGGCAAGCGGATGGCTGA
TGAAACCAAGCCAACCAGGGGTGATGCTGCCAACTTACTGATTTAGTGTATGATGGTGTTTTTGAGG
TGCTCCAGTGGCTTCTGTTTCTATCAGCTGTCCCTCCTGTTCAGCTACTGACGGGGTGGTGCGTAAC
GGCAAAAGCACCGCCGGACATCAGCGCTATCTCTGCTCTCACTGCCGTAAA
ACATGGCAACTGCAGTTCACTTACACCGCTTCTCAACCCGGTACGCACCAGAAAATCATTGATATGG
CCATGAATGGCGTTGGATGCCGGGCAACAGCCCGCATTATGGGCGTTGGCCTCAACA
```

Figure 4Bcontd.

```
CGATTTTACGTCACTTAAAAAACTCAGGCCGCAGTCGGTAACCTCGCGCATACAGCCGGGCAGTGAC
GTCATCGTCTGCGCGGAAATGGACGAACAGTGGGGCTATGTCGGGGCTAAATCGCGCCAGCGCTGGC
TGTTTTACGCGTATGACAGTCTCCGGAAGACGGTTGTTGCGCACGTATTCGGTGAACGCACTATGGC
GACGCTGGGGCGTCTTATGAGCCTGCTGTCACCCTTTGACGTGGTGATATGGATGACGGATGGCTGG
CCGCTGTATGAATCCCGCCTGAAGGGAAAGCTGCACGTAATCAGCAAGCGATATACGCAGCGAATTG
AGCGGCATAACCTGAATCTGAGGCAGCACCTGGCACGGCTGGGACGGAAGTCGCTGTCGTTCTCAAA
ATCGGTGGAGCTGCATGACAAAGTCATCGGGCATTATCTGAACATAAAACACTATCAATAAGTTGGA
GTCATTACCCAACCAGGAAGGGCAGCCCACCTATCAAGGTGTACTGCCTTCCAGACGAACGAAGAGC
GATTGAGGAAAAGGCGGCGGCGGCCGGCATGAGCCTGTCGGCCTACCTGCTGGCCGTCGGCCAGGGC
TACAAAATCACGGGCGTCGTGGACTATGAGCACGTCCGCGAGCTGGCCCGCATCAATGGCGACCTGG
GCCGCCTGGGCGGCCTGCTGAAACTCTGGCTCACCGACGACCCGCGCACGGCGCGGTTCGGTGATGC
CACGATCCTCGCCCTGCTGGCGAAGATCGAAGAGAAGCAGGACGAGCTTGGCAAGGTCATGATGGGC
GTGGTCCGCCCGAGGGCAGAGCCATGACTTTTTTAGCCGCTAAAACGGCCGGGGGGTGCGCGTGATT
GCCAAGCACGTCCCCATGCGCTCCATCAAGAAGAGCGACTTCGCGGAGCTGGTATTCGTGCAGGGCA
AGATTCGGAATACCAAGTACGAGAAGGACGGCCAGACGGTCTACGGGACCGACTTCATTGCCGATAA
GGTGGATTATCTGGACACCAAGGCACCAGGCGGGTCAAATCAGGAATAAGGGCACATTGCCCCGGCG
TGAGTCGGGGCAATCCCGCAAGGAGGGTGAATGAATCGGACGTTTGACCGGAAGGCATACAGGCAAG
AACTGATCGACGCGGGGTTTTCCGCCGAGGATGCCGAAACCATCGCAAGCCGCACCGTCATGCGTGC
GCCCCGCGAAACCTTCCAGTCCGTCGGCTCGATGGTCCAGCAAGCTACGGCCAAGATCGAGCGCGAC
AGCGTGCAACTGGCTCCCCCTGCCCTGCCCGCGCCATCGGCCGCCGTGGAGCGTTCGCGTCGTCTCG
AACAGGAGGCGGCAGGTTTGGCGAAGTCGATGACCATCGACACGCGAGGAACTATGACGACCAAGAA
GCGAAAAACCGCCGGCGAGGACCTGGCAAAACAGGTCAGCGAGGCCAAGCAGGCCGCGTTGCTGAAA
CACACGAAGCAGCAGATCAAGGAAATGCAGCTTTCCTTGTTCGATATTGCGCCGTGGCCGGACACGA
TGCGAGCGATGCCAAACGACACGGCCCGCTCTGCCCTGTTCACCACGCGCAACAAGAAAATCCCGCG
CGAGGCGCTGCAAAACAAGGTCATTTTCCACGTCAACAAGGACGTGAAGATCACCTACACCGGCGTC
GAGCTGCGGGCCGACGATGACGAACTGGTGTGGCAGCAGGTGTTGGAGTACGCGAAGCGCACCCCTA
TCGGCGAGCCGATCACCTTCACGTTCTACGAGCTTTGCCAGGACCTGGGCTGGTCG
ATCAATGGCCGGTATTACACGAAGGCCGAGGAATGCCTGTCGCGCCTACAGGCGACGGCGATGGGCT
TCACGTCCGACCGCGTTGGGCACCTGGAATCGGTGTCGCTGCTGCACCGCTTCCGCGTCCTGGACCG
TGGCAAGAAAACGTCCCGTTGCCAGGTCCTGATCGACGAGGAAATCGTCGTG
```

Figure 4B contd.

```
CTGTTTGCTGGCGACCACTACACGAAATTCATATGGGAGAAGTACCGCAAGCTGTCGCCGACGGCCC
GACGGATGTTCGACTATTTCAGCTCGCACCGGGAGCCGTACCCGCTCAAGCTGGAAACCTTCCGCCT
CATGTGCGGATCGGATTCCACCCGCGTGAAGAAGTGGCGCGAGCAGGTCGGCGAAGCCTGCGAAGAG
TTGCGAGGCAGCGGCCTGGTGGAACACGCCTGGGTCAATGATGACCTGGTGCATTGCAAACGCTAGG
GCCTTGTGGGGTCAGTTCCGGCTGGGGGTTCAGCAGCCAGCGCTTTACTGGCATTTCAGGAACAAGC
GGGCACTGCTCGACGCACTTGCTTCGCTCAGTATCGCTCGGGACGCACGGCGCGCTCTACGAACTGC
CGATAAACAGAGGATTAAAATTGACAATTGTGATTAAGGCTCAGATTCGACGGCTTGGAGCGGCCGA
CGTGCAGGATTTCCGCGAGATCCGATTGTCGGCCCTGAAGAAAGCTCCAGAGATGTTCGGGTCCGTT
TACGAGCACGAGGAGAAAAAGCCCATGGAGGCGTTCGCTGAACGGTTGCGAGATGCCGTGGCATTCG
GCGCCTACATCGACGGCGAGATCATTGGGCTGTCGGTCTTCAAACAGGAGGACGGCCCCAAGGACGC
TCACAAGGCGCATCTGTCCGGCGTTTTCGTGGAGCCCGAACAGCGAGGCCGAGGGGTCGCCGGTATG
CTGCTGCGGGCGTTGCCGGCGGGTTTATTGCTCGTGATGATCGTCCGACAGATTCCAACGGGAATCT
GGTGGATGCGCATCTTCATCCTCGGCGCACTTAATATTTCGCTATTCTGGAGCTTGTTGTTTATTTC
GGTCTACCGCCTGCCGGGCGGGGTCGCGGCGACGGTAGGCGCTGTGCAGCCGCTGATGG
TCGTGTTCATCTCTGCCGCTCTGCTAGGTAGCCCGATACGATTGATGGCGGTCCTGGGGGCTATTTG
CGGAACTGCGGGCGTGGCGCTGTTGGTGTTGACACCAAACGCAGCGCTAGATCCTGTCGGCGTCGCA
GCGGGCCTGGCGGGGGCGGTTTCCATGGCGTTCGGAACCGTGCTGACCCGCAAGTGGCAACCTCCCG
TGCCTCTGCTCACCTTTACCGCCTGGCAACTGGCGGCCGGAGGACTTCTGCTCGTTCCAGTAGCTTT
AGTGTTTGATCCGCCAATCCCGATGCCTACAGGAACCAATGTTCTCGGCCTGGCGTGGCTCGGCCTG
ATCGGAGCGGGTTTAACCTACTTCCTTTGGTTCCGGGGGATCTCGCGACTCGAACCTACAGTTGTTT
CCTTACTGGGCTTTCTCAGCCGGGATGGCGCTAAGAAGCTATTGCCGCCGATCTTCATATGCGGTGT
GAAATACCGCACAGATGCGTAAGGAGAAAATACCGCATCAGGCGCTCTTCCGCTTCCTCGCTCACTG
ACTCGCTGCGCTCGGTCGTTCGGCTGCGGCGAGCGGTATCAGCTCACTCAAAGGCGGTAATACGGTT
ATCCACAGAATCAGGGGATAACGCAGGAAAGAACATGTGAGCAAAAGGCCAGCAAAAGGCCAGGAAC
CGTAAAAAGGCCGCGTTGCTGGCGTTTTTCCATAGGCTCCGCCCCCTGACGAGCATCACAAAAATC
GACGCTCAAGTCAGAGGTGGCGAAACCCGACAGGACTATAAAGATACCAGGCGTTTCCCCCTGGAAG
CT
CCCTCGTGCGCTCTCCTGTTCCGACCCTGCCGCTTACCGGATACCTGTCCGCCTTTCTCCCTTCGGG
AAGCGTGGCGCTTTCTCATAGCTCACGCTGTAGGTATCTCAGTTCGGTGTAGGTCGTTCGCTCCAAG
CTGGGCTGTGTGCACGAACCCCCCGTTCAGCCCGACCGCTGCGCCTTATCCGGTAACTATCGTCTTG
AGTCCAACCCGGTAAGACACGACTTATCGCCACTGGCAGCAGCCACT
```

Figure 4B contd.

```
GGTAACAGGATTAGCAGAGCGAGGTATGTAGGCGGTGCTACAGAGTTCTTGAAGTGGTGGCCTAACT
ACGGCTACACTAGAAGGACAGTATTTGGTATCTGCGCTCTGCTGAAGCCAGTTACCTTCGGAAAAAG
AGTTGGTAGCTCTTGATCCGGCAAACAAACCACCGCTGGTAGCGGTGGTTTTTTTGTTTGCAAGCAG
CAGATTACGCGCAGAAAAAAAGGATATCAAGAAGATCCTTTGATCTTTTCTACGGGGTCTGACGCTC
AGTGGAACGAAAACTCACGTTAAGGGATTTTGGTCATGAGATTATCAAAAAGGATCTTCACCTAGAT
CCTTTTAAATTAAAAATGAAGTTTTAAATCAATCTAAAGTATATATGAGTAAACTTGGTCTGACAGT
TACCAATGCTTAATCAGTGAGGCACCTATCTCAGCGATCTGTCTATTTCGTTCATCCATAGTTGCCT
GACTCCCCGTCGTGTAGATAACTACGATACGGGAGGGCTTACCATCTGGCCCCAGTGCTGCAATGAT
ACCGCGAGACCCACGCTCACCGGCTCCAGATTTATCAGCAATAAACCAGCCAGCCGGAAGGGCCGAG
CGCAGAAGTGGTCCTGCAACTTTATCCGCCTCCATCCAGTCTATTAAACAAGTGGCAGCAACGGATT
CGCAAACCTGTCACGCCTTTTGTGCCAAAAGCCGCGCCAGGTTTGCGATCCGCTGTGCCAGGCGTTA
GGCGTCATATGAAGATTTCGGTGATCCCTGAGCAGGTGGCGGAAACATTGGATGCTGAGAACCATTT
CATTGTTCGTGAAGTGTTCGATGTGCACCTATCCGACCAAGGCTTTGAACTATCTACCAGAAGTGTG
AGCCCCTACCGGAAGGATTACATCTCGGATGATGACTCTGATGAAGACTCTGCTTGCTATGGCGCAT
TCATCGACCAAGAGCTTGTCGGGAAGATTGAACTCAACTCAACATGGAACGATCTAGCCTCTATCGA
ACACATTGTTGTCGCACACGCACCGAGGCAAAGGAGTCGCGCACAGTCTCATCGAATTTGCGAAA
AAGTGGGCACTAAGCAGACAGCTCCTTGGCATACGATTAGAGACACAAACGAACAATGTACCTGCCT
GCAATTTGTACGCAAAATGTGGCTTTACTCTCGGCGGCATTGACCTGTTCACGTATAAAACTAGACC
TCAAGTCTCGAACGAAACAGCGATGTACTGGTACTGGTTCTCGGGAGCACAGGATGACGCCTAACAA
TTCATTCAAGCCGACACCGCTTCGCGGCGCGGCTTAATTCAGGAGTTAAACATCATGAGGGAAGCGG
TGATCGCCGAAGTATCGACTCAACTATCAGAGGTAGTTGGCGTCATCGAGCGCCATCTCGAACCGAC
GTTGCTGGCCGTACATTTGTACGGCTCCGCAGTGGATGGCGGCCTGAAGCCACACAGTGATATTGAT
TTGCTGGTTACGGTGACCGTAAGGCTTGATGAAACAACGCGGCGAGCTTTGATCAACGACCTTTTGG
AAACTTCGGCTTCCCCTGGAGAGAGCGAGATTCTCCGCGCTGTAGAAGTCACCATTGTTGTGCACGA
CGACATCATTCCGTGGCGTTATCCAGCTAAGCGCGAACTGCAATTTGGAGAATGGCAGCGCAATGA
CATTCTTGCAGGTATCTTCGAGCCAGCCACGATCGACATTGATCTGGCTATCTTGCTGACAAAAGCA
AGAGAACATAGCGTTGCCTTGGTAGGTCCAGCGGCGGAGGAACTCTTTGATCCGGTTCCTGAACAGG
ATCTATTTGAGGCGCTAAATGAAACCTTAACGCTATGGAACTCGCCGCCCGA
CTGGCTGGCCGATGAGCGAAATGTAGTGCTTACGTTGTCCCGCATTTGGTACAGCGCAGTAACCGGC
AAAATCGCGCCGAAGGATGTCGCTGCCGACTGGGCAATGGAGCGCCTGCCGGCCCAG
```

Figure 4B contd.

```
TATCAGCCCGTCATACTTGAAGCTAGGCAGGCTTATCTTGGACAAGAAGATCGCTTGGCCTCGCGCG
CAGATCAGTTGGAAGAATTTGTTCACTACGTGAAAGGCGAGATCACCAAGGTAGTCGGCAAATAATG
TCTAACAATTCGTTCAAGCCGACGCCGCTTCGCGGCGCGGCTTAACTCAAGCGTTAGAGAGCTGGGG
AAGACTATGCGCGATCTGTTGAAGGTGGTTCTAAGCCTCGTACTTGCGATGGCATCGGGGCAGGCAC
TTGCTGACCTGCCAATTGTTTTAGTGGATGAAGCTCGTCTTCCCTATGACTACTCCCCATCCAACTA
CGACATTTCTCCAAGCAACTACGACAACTCCATAAGCAATTACGACAATAGTCCATCAAATTACGAC
AACTCTGAGAGCAACTACGATAATAGTTCATCCAATTACGACAATAGTCGCAACGGAAATCGTAGGC
TTATATATAGCGCAAATGGGTCTCGCACTTTCGCCGGCTACTACGTCATTGCCAACAATGGGACAAC
GAACTTCTTTTCCACATCTGGCAAAAGGATGTTCTACACCCCAAAAGGGGGCGCGGCGTCTATGGC
GGCAAAGATGGGAGCTTCTGCGGGGCATTGGTCGTCATAAATGGCCAATTTTCGCTTGCCCTGACAG
ATAACGGCCTGAAGATCATGTATCTAAGCAACTAGCCTGCTCTCTAATAAAATGTTAGGAGCTTGGC
TGCCATTTTTGGGGTGAGGCCGTTCGCGGCCGAGGGGCGCAGCCCCTGGGGGGATGGGAGGCCCGCG
TTAGCGGGCCGGGAGGGTTCGAGAAGGGGGGGCACCCCCCTTCGGCGTGCGCGGTCACGCGCACAGG
GCGCAGCCCTGGTTAAAAACAAGGTTTATAAATATTGGTTTAAAAGCAGGTTAAAAGACAGGTTAGC
GGTGGCCGAAAAACGGGCGGAAACCCTTGCAAATGCTGGATTTTCTGCCTGTGGACAGCCCCTCAAA
TGTCAATAGGTGCGCCCCTCATCTGTCAGCACTCTGCCCCTCAAGTGTCAAGGATCGCGCCCCTCAT
CTGTCAGTAGTCGCGCCCCTCAAGTGTCAATACCGCAGGGCACTTATCCCCAGGCTTGTCCACATCA
TCTGTGGGAAACTCGCGTAAAATCAGGCGTTTTCGCCGATTTGCGAGGCTGGCCAGCTCCACGTCGC
CGGCCGAAATCGAGCCTGCCCCTCATCTGTCAACGCCGCGCCGGGTGAGTCGGCCCCTCAAGTGTCA
ACGTCCGCCCCTCATCTGTCAGTGAGGGCCAAGTTTTCCGCGAGGTATCCACAACGCCGGCGGCCGG
CCGCGGTGTCTCGCACACGGCTTCGACGGCGTTTCTGGCGCGTTTGCAGGGCCATAGACGGCCGCCA
GCCCAGCGGCGAGGGCAACCAGCCCGGTGAGCGTCGGAAAGGGTCGACGATCTTGCTGCGTTCGGAT
ATTTTCGTGGAGTTCCCGCCACAGACCCGGATTGAAGGCGAGATCCAGCAACTCGCGCCAGATCATC
CTGTGACGGAACTTTGGCGCGTGATGACTGGCCAGGACGTCGGCCGAAAGAGCGACAAGCAGATCAC
GCTT
TTCGACAGCGTCGGATTTGCGATCGAGGATTTTTCGGCGCTGCGCTACGTCCGCGACCGCGTTGAGG
GATCAAGCCACAGCAGCCCACTCGACCTTCTAGCCGACCCAGACGAGCCAAGGGATCTTTTTGGAAT
GCTGCTCCGTCGTCAGGCTTTCCGACGTTTGGGTGGTTGAACAGAAGTCATT
ATCGCACGGAATGCCAAGCACTCCCGAGGGGAACCCTGTGGTTGGCATGCACATACAAATGGACGAA
CGGATAAACCTTTTCACGCCCTTTTAAATATCCGATTATTCTAATAAACGCTCTTTTCTCTTAGGTT
TACCCGCCAATATATCCTGTCAAACACTGATAGTTTAAACTGAAGGCGGGAA
```

Figure 4B contd.

```
ACGACAATCTGATCATGAGCGGAGAATTAAGGGAGTCACGTTATGACCCCCGCCGATGACGCGGGAC
AAGCCGTTTTACGTTTGGAACTGACAGAACCGCAACGTTGAAGGAGCCACTCAGCCGCGGTGGCGGC
CGCAGTACTGAGCTTCGAGACAAGTTTGTACAAAAAAGCAGGCTCATGATTAGTTAGATCAAGCTTT
TGAGTCTTCAAAAACATAAAAATTACAAAAAAAAAACAAACTTAAAATCATTTATCAATTTGAACAA
CAAAGCTTGGCCGAATGCTAAGAGCTTAAAAATGGCTTCTTTTGTTTCTTTTTGTTGCAAACGGTGG
AGAGAAGAGGGAAATGAAGATTGACCATATTTTTTATTATGTTTTAACATATAATATTAATAATTT
AATCATAATTATACTTTGGTGAATGTGACAGTGGGGAGATACGTAAAGTATATAACATTATACTTTT
TGCAAGCAGTTGGCTGGTCTACCCAAGAGTGATCAAAGTTTGAGCTGCCTTCAATGAGCCAATTTTT
GCCCATAATGGATAAAGGCAATTTGTTTAGTTCAACTGCTCACAGAATAATGTTAAAATGAAATTAA
AATAAGGTGGCCTGGTCACACACACAAAAAAAAACTAATGTTGGTTGGTTGAATTTTATATTACGGA
ATGTAATATTATATTTTAAAATAAAATTATGTTATTTAGATTCTTAATATTTTGAGCATTCCATACT
ATAATTTCGTATACATAATATTAAAATATAGTAATATAAAGTGTAATTAACTTTAAATTACAAGCAT
AA
TATTAAATTTTGAATCAATTAATTTTTATTTCTATTATTTTAATTAATTTAGTCTATTTTTTCAAAA
TAAAATTTAAATCTAAATAAAAATAATTTTTCCTTAATGTTGAAACAACTCATGTTATACTTCAAAA
TTATAAGTATTATATTTACCTTGATGATTTATTTATTAGTATATTAATTCTGATTATAATTATGGTG
GGATACAATCGCTTTCCACTAAATATTTTAACTATGATTTATAAATTTATTTCAACATCGTATATTT
ACTTATTAATACATAATTTATCATAATTTTATGGAAATTGAGACCAAGAAACATTAAGAGAACAAAT
TCTATAACAAAGACAATTTAGAAAAAAATGTACTTTTAGGTAATTTTAAGTACTCTTAACCAAACAC
AAAAATTCAAATCAAATGAACTAAATAAGATAATATAACATACGGAACATCTTACTTGTAATCTTAC
ATTCCCATAATTTTATTATGAAAATAATCTTATATTACTCGAACTAAATGTTGTCACAAATTATTA
TCTAAATAAAGAAAAACACTTAATTTTTATAACATTTTTTCATATATTTGAAAGATTATATTTTGTA
TATTTACGTAAAAATATTTGACATAGATTGAGCACCTTCTTAACATAATCCCACCATAAGTCAAGTA
TGTAGATGAGAAATTGGTACAAACAACGTGGGGCCAAATCCCACCAAACCATCTCTCATTCTCTCCT
ATAAAAGGCTTGCTACACATAGACAACAATCCACACACAAATACACGTTCTTTTCTTTCTATTTGAT
TAACCACCCAGCTTTC
```

FIBER-PREFERENTIAL PROMOTER IN COTTON

CROSS REFERENCE TO RELATED APPLICATION

This application claims the benefit of U.S. Provisional Application Ser. No. 61/540,055, filed Sep. 28, 2011, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "112013Sequencelisting.txt", created on Sep. 27, 2012, and having a size of 8 kilobytes and is filed concurrently with the specification. A replacement sequence listing is submitted electronically via EFS-Web on May 31, 2013 as an ASCII formatted sequence listing with a file named "112013_ReplacementSequenceListing.txt", created on May 31, 2013 and having a size of 32,000 bytes. The sequence listing contained in this ASCII formatted document is part of the specification and is herein incorporated by reference in its entirety.

FIELD OF THE INVENTION

The present invention relates to materials and methods for the expression of a gene of interest preferentially or selectively in fibers of plants, such as cotton plants. In particular, the invention provides an expression cassette for regulating fiber-preferential or fiber-selective expression in cotton plants.

INTRODUCTION TO THE INVENTION

Cotton fiber is the single most important textile worldwide. About 80 million acres of cotton are harvested annually across the globe. Cotton is the fifth largest crop in the U.S. in terms of acreage production, with an average of 10.3 million acres planted in the years 2006 to 2008. About 90% of cotton grown worldwide is *Gossypium hirsutum* L., whereas *Gossypium barbadense* accounts for about 8%. Consequently, the modification of cotton fiber characteristics to better suit the requirements of the industry and the consumer is a major effort in breeding by either classical methods or by genetically altering the genome of cotton plants. Goals to be achieved include increased lint fiber length, strength, dyability, decreased fuzz fiber production, fiber maturity ratio, immature fiber content, fiber uniformity and micronaire.

Cotton fiber development is a multistage process under the regulation of a vast number of genes, many of which are up-regulated or highly expressed in developing fiber cells (Li, C. H. et al., 2002; Ruan et al., 2003; Wang, S. et al., 2004; Li et al., 2005; Luo et al., 2007).

Each cotton fiber is a differentiated single epidermal cell of the ovule. Approximately half a million fibers are produced per cotton boll, some forming fuzz and some forming lint. Initiation of an epidermal cell into fiber requires a change in cell fate, which is a fundamental biological process involving genetic, physiological and developmental "switches". Genetic mutations, polyploidy, pollination/fertilization, and hormonal regulation can affect the number of cells developing into fibers or alter fiber cell properties (fuzz vs. lint). However, it is unclear how these factors control gene expression changes that orchestrate the pattern and tempo in early stages of fiber development.

In contrast, the morphological development of cotton fibers is well documented in the art. Cotton fibers undergo four overlapping developmental stages: fiber cell initiation, elongation, secondary wall biosynthesis, and maturation. Fiber initiation is a rapid process. The white fluffy fibers begin to develop immediately after anthesis and continue up to 3 days post-anthesis (DPA), which is followed by fiber cell elongation (until 20 DPA). Secondary wall biosynthesis initiates around 15 dpa and continues to 35 DPA, followed by a maturation process until 45-60 DPA. Cotton fibers are derived from ovular epidermal cells (maternal tissues). However, only ~25-30% of the epidermal cells differentiate into the commercially important lint fibers. The majority of cells does not differentiate into fibers or develop into short fibers or fuzz. For the cells committed to fiber development, cell initiation and elongation are nearly synchronous on each ovule, indicating that changes in gene expression are orchestrated during fiber differentiation and development through intercellular signaling and/or timing mechanisms.

Various promoters driving expression of genes in the cotton seed have been described. Various promoters driving fiber-preferential expression in cotton are also known.

E6 was the first cotton fiber gene identified, and the E6 promoter has been used for engineering cotton fiber quality (John and Keller, 1996). GhRDL1, a gene highly expressed in cotton fiber cells at the elongation stage, encodes a BURP domain containing protein (Li, C. H. et al., 2002), and the GaRDL1 promoter exhibited a trichome-specific activity in transgenic *Arabidopsis* plants (Wang, S. et al., 2004). GhTUB1 transcripts preferentially accumulate at high levels in fiber, accordingly, the pGhTUB1::GUS fusion gene was expressed at a high level in fiber but at much lower levels in other tissues (Li, X. B. et al., 2002). Promoters of three cotton lipid transfer protein genes, LTP3, LTP6, and FSltp4, were able to direct GUS gene expression in leaf and stem glandular secretory trichomes (GSTs) in transgenic tobacco plants (Hsu et al., 1999; Liu et al., 2000; Delaney et al., 2007), however, they did not exhibit a clear tissue-specificity. For example, in pFSltp4::GUS transgenic tobacco plants, strong GUS activity could be detected in all types of trichomes; in addition, GUS expression was also visible at the leaf margin, vascular tissue, ovules, and root tips (Delaney et al., 2007).

The cotton R2R3 MYB transcription factor GaMYB2 has been shown to be a functional homologue of *Arabidopsis* GLABRA1 (GL1), a key regulator of *Arabidopsis* trichome formation. GaMYB2 is expressed in cotton fiber cells at the early developmental stages (Wang, S. et al., 2004). Its promoter drives trichome-specific expression also in *Arabidopsis* and GST headspecific expression in tobacco (Shangguan et al., 2008).

U.S. Pat. No. 7,626,081 discloses a cotton seed-specific promoter found in the alpha globulin gene. The promoter Gh-sp is derived from a seed protein gene and is active only in maturing cotton seeds (Song et al., 2000).

US patent application 2003/0106089 discloses a gene expressed in a fiber-specific manner and its promoter. U.S. Pat. No. 6,211,430 discloses a promoter directing expression in late fiber development.

Despite there now being many promoters known to drive seed-preferential or fiber-preferential expression in cotton plants, it would be desirable to have further fiber-preferential promoters available for fiber-preferential expression in cotton.

SUMMARY OF THE INVENTION

The present application discloses an isolated nucleic acid comprising (a) at least 700 consecutive nucleotides of SEQ ID NO: 1; (b) a nucleotide sequence with at least 80% sequence identity to the nucleotide sequence of (a); (c) a nucleotide sequence hybridizing under stringent conditions to the nucleotide sequence of (a) or (b); and (d) a nucleotide sequence complementary to the nucleotide sequence of any one of (a) to (c). In some embodiments, said isolated nucleic acid may have fiber-preferential promoter activity. Further disclosed herein is a chimeric gene comprising the isolated nucleic acid described herein operably linked to a nucleic acid coding for an expression product of interest, and a transcription termination and polyadenylation sequence. Also disclosed herein are a vector, a transgenic plant cell, a transgenic plant and a seed as characterized in the claims. Methods disclosed herein relate to the production of a transgenic plant, growing cotton, producing a seed, effecting fiber-preferential expression of a product in cotton and of altering fiber properties in a cotton plant as characterized in the claims.

DETAILED DESCRIPTION OF THE INVENTION

General Comments

In this specification, a number of documents including patent applications and manufacturer's manuals are cited. The disclosure of these documents, while not considered relevant for the patentability of this invention, is hereby incorporated by reference in its entirety. More specifically, all referenced documents are incorporated by reference to the same extent as if each individual document was specifically and individually indicated to be incorporated by reference.

As used herein, the term "comprising" is to be interpreted as specifying the presence of the stated features, integers, steps or components as referred to, but does not preclude the presence or addition of one or more features, integers, steps or components, or groups thereof. Thus, e.g., a nucleic acid comprising a sequence of nucleotides, may comprise more nucleotides than the actually cited ones, i.e., be embedded in a larger nucleic acid. A chimeric gene as will be described further below which comprises a nucleic acid which is functionally or structurally defined may comprise additional nucleic acids etc. However, in context with the present disclosure, the term "comprising" also includes "consisting of".

In other words, the terminology relating to a nucleic acid "comprising" a certain nucleotide sequence, as used throughout the text, refers to a nucleic acid or protein including or containing at least the described sequence, so that other nucleotide or amino acid sequences can be included at the 5' (or N-terminal) and/or 3' (or C-terminal) end, e.g. (the nucleotide sequence of) a selectable marker protein, (the nucleotide sequence of) a transit peptide, and/or a 5' leader sequence or a 3' trailer sequence.

Nucleic Acids

In one aspect, the present application discloses an isolated nucleic acid comprising (a) at least 700 consecutive nucleotides of SEQ ID NO: 1; (b) a nucleotide sequence with at least 80% sequence identity to the nucleotide sequence of (a); (c) a nucleic acid sequence hybridizing under stringent conditions to the nucleotide sequence of (a) or (b); and (d) a nucleic acid sequence complementary to the nucleotide sequence of any one of (a) to (c).

In another aspect, the present application discloses an isolated nucleic acid comprising (a) at least 700 consecutive nucleotides of SEQ ID NO: 1; (b) a nucleotide sequence with at least 80% sequence identity to the nucleotide sequence of (a); (c) a nucleic acid sequence hybridizing under stringent conditions to the nucleotide sequence of (a) or (b); and (d) a nucleic acid sequence complementary to the nucleotide sequence of any one of (a) to (c), wherein said isolated nucleic acid has fiber-preferential promoter activity.

The isolated nucleic acid of this aspect is hereinafter also denoted the "promoter sequence".

Unless indicated otherwise, the embodiments described below for the promoter sequence disclosed herein are also applicable to respective embodiments of other aspects disclosed herein.

Nucleic acids can be DNA or RNA, single- or double-stranded. Nucleic acids can be synthesized chemically or produced by biological expression in vitro or in vivo.

Nucleic acids can be chemically synthesized using appropriately protected ribonucleoside phosphoramidites and a conventional DNA/RNA synthesizer. Suppliers of RNA synthesis reagents are Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK).

In connection with the chimeric gene of the present disclosure, DNA includes cDNA and genomic DNA.

An "isolated nucleic acid" or "isolated nucleic acid sequence", as used in the present application, refers to a nucleic acid as defined above which is not naturally-occurring, such as, for example, an artificial or synthetic nucleic acid with a different nucleotide sequence than the naturally-occurring nucleic acid or a nucleic acid which is shorter than a naturally occurring one, or which is no longer in the natural environment wherein it was originally present, e.g., a nucleic acid coding sequence associated with a heterologous regulatory element such as a bacterial coding sequence operably-linked to a plant-expressible promoter, or in a chimeric gene or a nucleic acid transferred into another host cell, such as a transgenic plant cell.

In one embodiment, the length of the isolated nucleic acid sequence of the invention, such as, e.g., a fragment of SEQ ID NO: 1 as disclosed herein, and its position within SEQ ID NO: 1 is to be chosen such that it is sufficiently long, e.g. comprising all elements necessary and sufficient, and positioned such that it is capable of inducing fiber-preferential expression.

Methods of evaluating whether a nucleic acid sequence as described above, which in the present application represents a promoter sequence, is capable of inducing expression of a chimeric gene it is comprised in or, in particular, of a nucleic acid sequence operably linked thereto, in a fiber-preferential manner are known to the skilled person.

For example reporter gene studies may be performed in order to evaluate the expression inducing function of a nucleic acid sequence. This includes operably linking the nucleic acid sequence of the invention to a reporter gene such as GUS, introducing the resulting nucleic acid construct in a plant or plant cell, such as in a cotton plant, and evaluating induction of the expression of said reporter gene in different tissues of said plant, as will also be described in more details further below.

Said fragment of the nucleic acid sequence described herein which in some embodiments may have fiber-preferential promoter activity in some examples may accordingly comprise at least 700, at least 800, at least 900, at least 1000, at least 1100, at least 1200, at least 1300 or at least 1400 consecutive nucleotides of SEQ ID NO: 1. In another example, said nucleic acid comprises the nucleic acid sequence of SEQ ID NO: 1. In yet another example, said promoter sequence consists of the nucleic acid sequence of SEQ ID NO: 1.

However, it will be clear that variants of the present nucleic acid, including insertions, deletions and substitutions thereof may also be used to the same effect. Generally, such variants have at least 80%, at least 90%, at least 95% or even at least 98% sequence identity to SEQ ID NO: 1. In some embodiment, such variants may retain their fiber-preferential promoter activity.

As used herein, the term "promoter" denotes any nucleic acid sequence, such as a DNA sequence, which is recognized and bound (directly or indirectly) by a DNA-dependent RNA-polymerase during initiation of transcription, resulting in the generation of an RNA molecule that is complementary to the transcribed DNA. This region may also be referred to as a "5' regulatory region". Promoters are usually located upstream of the 5' untranslated region (UTR) preceding the protein coding sequence to be transcribed and have regions that act as binding sites for RNA polymerase II and other proteins such as transcription factors to initiate transcription of an operably linked sequence. Promoters may themselves contain sub-elements (i.e. promoter motifs) such as cis-elements or enhancer domains that regulate the transcription of operably linked genes. The promoter and a connected 5' UTR are also denoted as "promoter region".

A "fiber-preferential" promoter in the context of the present invention means that the transcription of a nucleic acid sequence controlled by a promoter is at least 2 times higher, at least 5 times higher, at least 10 times higher, or even 20 times higher in a fiber cell than in cells of another plant tissue such as, for example, leaf tissue. The term does not take into account potential wound-induced expression. In other words, fiber-preferential expression may still be present even if the promoter of the invention is induced upon wounding of a plant.

In some embodiments, the promoter of the present invention may also be fiber specific. In connection with the present invention, a "fiber-specific" promoter means that the transcription of a nucleic acid controlled by said promoter is more than 20 times higher, such as at least 30 times higher, at least 40 times higher, at least 50 times higher or even 100 times higher in a fiber cell than on average in the cells of other plant tissues of the time of fiber development, such as from 1 dpa until 60 dpa, such as from 10 to 50, from 20 to 50 dpa, from 10 to 35, from 10 to 30 or from 15 to 30 dpa or 15 to 35 dpa. The term does not take into account potential wound-induced expression. In other words, fiber-specific expression may still be present even if the promoter of the invention is induced upon wounding of a plant.

Confirmation of promoter activity for a promoter sequence or a functional promoter fragment may be determined by those skilled in the art, for example using a promoter-reporter construct comprising the promoter sequence operably linked to an easily scorable marker as herein further explained. The fiber-preferential expression capacity of the identified or generated fragments or variants of the promoter described herein can be conveniently tested by operably linking such nucleic acid sequences to a nucleotide sequence encoding an easily scorable marker, e.g. a beta-glucuronidase gene, introducing such a chimeric gene into a plant and analyzing the expression pattern of the marker in fiber cells as compared to the expression pattern of the marker in other parts of the plant. Other candidates for a marker (or a reporter gene) are chloramphenicol acetyl transferase (CAT), beta-galactosidase (beta-GAL), and proteins with fluorescent or phosphorescent properties, such as green fluorescent protein (GFP) from *Aequora victoria* or luciferase. To confirm promoter function, a nucleic acid sequence representing the promoter is operably linked to the coding sequence of a marker (reporter) gene by recombinant DNA techniques well known in the art. The reporter gene is operably linked downstream of the promoter, so that transcripts initiating at the promoter proceed through the reporter gene. The expression cassette containing the reporter gene under the control of the promoter can be introduced into an appropriate cell type by transformation techniques well known in the art and described elsewhere in this application. To assay for the reporter protein, cell lysates are prepared and appropriate assays, which are well known in the art, for the reporter protein are performed. For example, if CAT were the reporter gene of choice, the lysates from cells transfected with constructs containing CAT under the control of a promoter under study are mixed with isotopically labeled chloramphenicol and acetyl-coenzyme A (acetyl-CoA). The CAT enzyme transfers the acetyl group from acetyl-CoA to the 2- or 3-position of chloramphenicol. The reaction is monitored by thin-layer chromatography, which separates acetylated chloramphenicol from unreacted material. The reaction products are then visualized by autoradiography. The level of enzyme activity corresponds to the amount of enzyme that was made, which in turn reveals the level of expression and the fiber-preferential functionality of the promoter or fragment or variant thereof. This level of expression can also be compared to other promoters to determine the relative strength of the promoter under study. Once activity and functionality is confirmed, additional mutational and/or deletion analyses may be employed to determine e.g. a minimal promoter region and/or sequences required to initiate transcription. Thus, sequences can be deleted at the 5' end of the promoter region and/or at the 3' end of the promoter region, or within the promoter sequence and/or nucleotide substitutions may be introduced. These constructs are then again introduced into cells and their activity and/or functionality are determined.

Instead of measuring the activity of a reporter enzyme, the transcriptional promoter activity (and functionality) can also be determined by measuring the level of RNA that is produced. This level of RNA, such as mRNA, can be measured either at a single time point or at multiple time points and as such the fold increase can be average fold increase or an extrapolated value derived from experimentally measured values. As it is a comparison of levels, any method that measures mRNA levels can be used. In an example, the tissue or organs compared are a seed or seed tissue such as fibers with a leaf or leaf tissue. In another example, multiple tissues or organs are compared. One example for multiple comparisons is fiber cells compared with 2, 3, 4, or more tissues or organs selected from the group consisting of floral tissue, floral apex, pollen, leaf, embryo, shoot, leaf primordia, shoot apex, root, root tip, vascular tissue and cotyledon. As used herein, examples of plant organs are seed, leaf, root, etc. and example of tissues are leaf primordia, shoot apex, vascular tissue, etc. The activity or strength of a promoter may be measured in terms of the amount of mRNA or protein accumulation it specifically produces, relative to the total amount of mRNA or protein. The promoter expresses an operably linked nucleic acid sequence for example at a level greater than about 0.1%, about 0.2%, greater than about 0.5, 0.6, 0.7, 0.8, or about 0.9%, greater than about 1%, 2%, 3%, 4%, 5%, 6%, 7%, 8%, or about 9%, or greater than about 10% of the total mRNA of the cell it is contained in. Alternatively, the activity or strength of a promoter may be expressed relative to a well-characterized promoter for which transcriptional activity was previously assessed.

In another aspect, fiber-preferential promoters are provided which comprise a nucleic acid sequence having at least 80%, at least 90%, at least 95% or at least 98% sequence identity to SEQ ID NO: 1 or a fragment thereof as defined above, such as, for example, a nucleic acid comprising at least 700, at least 800, at least 900, at least 1000, at least 1100, at least 1200, at least 1300 or at least 1400 consecutive nucleotides of the nucleotide sequence set forth as SEQ ID NO: 1. Naturally occurring variants of the promoter disclosed herein can be identified with the use of well-known molecular biology techniques, such as, for example, with polymerase chain reaction (PCR) and hybridization techniques as herein outlined before. Such nucleic acid sequences also include synthetically derived nucleic acid sequences, such as those generated, for example, by using site-directed mutagenesis of SEQ ID NO: 1 or a fragment thereof. Generally, nucleic acid sequence variants of the invention will have at least 80%, e.g., 81% to 84%, at least 85%, e.g., 86%, 87%, 88%, 89%, 90%, 91%, 92%, 93%, 94%, 95%, 96%, 97%, to 98% and 99% sequence identity to the nucleic acid sequence of SEQ ID NO: 1 or a fragment thereof as defined above, such as, for example, a nucleic acid comprising at least 700, at least 800, at least 900, at least 1000, at least 1100, at least 1300 or at least 1400 at least 1200 consecutive nucleotides of the nucleotide sequence set forth as SEQ ID NO: 1. Derivatives of the nucleic acid sequences disclosed herein may include, but are not limited to, deletions of sequence, single or multiple point mutations, alterations at a particular restriction enzyme recognition site, addition of functional elements, or other means of molecular modification which may enhance, or otherwise alter promoter expression. Techniques for obtaining such derivatives are well-known in the art (see, for example, J. F. Sambrook, D. W. Russell, and N. Irwin (2000) Molecular Cloning: A Laboratory Manual). For example, one of ordinary skill in the art may delimit the functional elements within the promoters disclosed herein and delete any non-essential elements. Functional elements may be modified or combined to increase the utility or expression of the sequences of the invention for any particular application. Those of skill in the art are familiar with the standard resource materials that describe specific conditions and procedures for the construction, manipulation, and isolation of macromolecules (e.g., DNA molecules, plasmids, etc.), as well as the generation of recombinant organisms and the screening and isolation of DNA molecules.

The promoter sequence of SEQ ID NO: 1 and its functional fragments and variants may for example be altered to contain "enhancer DNA" to assist in elevating gene expression. As is well-known in the art, certain DNA elements can be used to enhance the transcription of DNA as part of or in association with a promoter. These enhancers are often found upstream (5') to the start of transcription in a promoter that functions in eukaryotic cells, but can be inserted downstream (3') to the coding sequence. In some instances, these enhancer DNA elements are within or part of introns. Among the introns that are useful as enhancer DNA are the 5' introns from the rice actin 1 gene (see U.S. Pat. No. 5,641,876), the rice actin 2 gene, the maize alcohol dehydrogenase gene, the maize heat shock protein 70 gene (see U.S. Pat. No. 5,593,874), the maize shrunken 1 gene, the light sensitive 1 gene of *Solanum tuberosum*, and the heat shock protein 70 gene of *Petunia hybrida* (see U.S. Pat. No. 5,659,122). Thus, as contemplated herein, a promoter or promoter region includes variations of promoters derived by inserting or deleting regulatory regions, subjecting the promoter to random or site-directed mutagenesis etc. The activity or strength of a promoter may be measured in terms of the amounts of RNA it produces, or the amount of protein accumulation in a cell or tissue, relative to a promoter whose transcriptional activity has been previously assessed, as described above.

As used herein, the term "percent sequence identity" refers to the percentage of identical nucleotides between two segments of a window of optimally aligned DNA. Optimal alignment of sequences for aligning a comparison window are well-known to those skilled in the art and may be conducted by tools such as the local homology algorithm of Smith and Waterman (Waterman, M. S., Chapman & Hall. London, 1995), the homology alignment algorithm of Needleman and Wunsch (1970), the search for similarity method of Pearson and Lipman (1988), and preferably by computerized implementations of these algorithms such as GAP, BESTFIT, FASTA, and TFASTA available as part of the GCG (Registered Trade Mark), Wisconsin Package (Registered Trade Mark from Accelrys Inc., San Diego, Calif.). An "identity fraction" for aligned segments of a test sequence and a reference sequence is the number of identical components that are shared by the two aligned sequences divided by the total number of components in the reference sequence segment, i.e., the entire reference sequence or a smaller defined part of the reference sequence. Percent sequence identity is represented as the identity fraction times 100. The comparison of one or more DNA sequences may be to a full-length DNA sequence or a portion thereof, or to a longer DNA sequence.

The term "hybridization" refers to the ability of a first strand of nucleic acid to join with a second strand via hydrogen bond base pairing when the two nucleic acid strands have sufficient sequence identity. Hybridization occurs when the two nucleic acid molecules anneal to one another under appropriate conditions. Nucleic acid hybridization is a technique well known to those of skill in the art of DNA manipulation. The hybridization property of a given pair of nucleic acids is an indication of their similarity or identity. Another indication that two nucleic acid sequences are largely identical is that the two molecules hybridize to each other under stringent conditions. "Stringent hybridization conditions" and "stringent hybridization wash conditions" in the context of nucleic acid hybridization experiments such as Southern and Northern hybridization are sequence dependent, and are different under different environmental parameters. An example of highly stringent wash conditions is 0.1×SSC, 5×Denhardt's solution, 0.5% SDS at 65° C. for e.g. about 15 minutes. An example of appropriate wash conditions for the present invention is a 2×SSC, 0.1% SDS wash at 65° C. for e.g. about 15 minutes. Often, a high stringency wash is preceded by a low stringency wash to remove background probe signal. Stringent conditions may also be achieved with the addition of destabilizing agents such as formamide. In general, a signal to noise ratio of 2× (or higher) than that observed for an unrelated probe in the particular hybridization assay indicates detection of a specific hybridization. Very stringent conditions are selected to be equal to the Tm for a particular probe.

In the course of the present invention, a fiber-preferential promoter, together with a subsequent 5' UTR (together also denoted as "promoter region") has been identified in *Gossypium hirsutum*. Said promoter controls an Fb8-like gene in cotton.

The promoter is highly expressed in fibers. It has been shown that expression is particularly strong during the cell thickening stage of fiber development; expression of the gene product was detected from 20 to 35 dpa.

It is expected that the current promoter will be suitable for fiber-preferential expression at least during later stages of developing fibers of transgenes in cotton. The current promoter can be used to express genes which modify cotton fiber properties, especially properties of the cotton fiber cell wall.

In a particular embodiment the fiber-preferential promoter is a promoter expressing during the fiber elongation stage starting from about 10 dpa till the end of the cell wall thickening phase of the fiber at about 30 to 35 dpa. In yet another embodiment, the fiber-preferential promoter is a promoter expressing during secondary cell wall deposition at about 30 dpa.

Unless indicated otherwise, the specific definitions or specific features of certain examples disclosed in the present application in connection with one aspect can be introduced into any other aspect disclosed herein.

In some embodiments, the nucleic acid sequence of the present promoter as well as fragments and variants thereof as defined above exert fiber-preferential promoter activity.

In one example, the fiber-preferential promoter activity is in cotton.

In one example said isolated nucleic acid is not longer than 1437 nucleotides. In another example of an isolated nucleic acid being not longer than 1437 nucleotides said nucleic acid sequence has fiber-preferential promoter activity.

In one example of a nucleic acid sequence with fiber-preferential promoter activity, said activity occurs at least between 10 and 20 dpa, between 10 and 25 dpa, between 10 and 30 dpa or between 10 and 35 dpa.

Chimeric Genes

In another aspect, the present application discloses a chimeric gene comprising the isolated nucleic acid described herein operably linked to a nucleic acid sequence coding for an expression product of interest, and a transcription termination and polyadenylation sequence functional in plant cells.

A chimeric gene is an artificial gene constructed by operably linking fragments of unrelated genes or other nucleic acid sequences. In other words "chimeric gene" denotes a gene which is not normally found in a plant species or refers to any gene in which the promoter, adjoined parts of the promoter or one or more other regulatory regions of the gene are not associated in nature with a part or all of the transcribed nucleic acid, i.e. are heterologous with respect to the transcribed nucleic acid. More particularly, a chimeric gene is an artificial, i.e. non-naturally occurring, gene produced by an operable linkage of the nucleic acid sequence of the invention, such as e.g. the nucleic acid of SEQ ID NO: 1, a fragment thereof or a nucleic acid sequence having at least 80% sequence identity thereto, all capable of directing fiber-preferential expression of an expression product of interest as described above, with a second nucleic acid sequence encoding said expression product of interest which is not naturally operably linked to said nucleic acid sequence.

The term "heterologous" refers to the relationship between two or more nucleic acid or protein sequences that are derived from different sources. For example, a promoter is heterologous with respect to an operably linked nucleic acid sequence, such as a coding sequence, if such a combination is not normally found in nature. In addition, a particular sequence may be "heterologous" with respect to a cell or organism into which it is inserted (i.e. does not naturally occur in that particular cell or organism). For example, the chimeric gene disclosed herein is a heterologous nucleic acid.

The term "operably linked" refers to the functional spatial arrangement of two or more nucleic acid regions or nucleic acid sequences. For example, a promoter region may be positioned relative to a nucleic acid sequence encoding an expression product of interest such that transcription of said nucleic acid sequence is directed by the promoter region. Thus, a promoter region is "operably linked" to the nucleic acid sequence.

The promoter, fragment or variant thereof as described above may be operably linked to a nucleic acid sequence encoding an expression product of interest that is heterologous with respect to the promoter. The nucleic acid sequence may generally be any nucleic acid sequence for which an altered level such as an increased level of transcription is desired. The nucleic acid sequence can for example encode a polypeptide that is capable of modifying fiber properties in cotton.

Suitable heterologous nucleic acid sequences for modifying the properties of cotton fibers include, without limitation, those disclosed in WO02/45485 whereby fiber quality in fiber producing plants, such as cotton, is modified by modulating sucrose synthase activity and/or expression in such plants, the nucleic acids useful for improving fiber strength or for introducing positive charges into the plant cell wall as described in WO2006/136351 or WO2011/089021.

An "expression product" denotes an intermediate or end product arising from the transcription and optionally translation of the nucleic acid, such as DNA or RNA, coding for such product. During the transcription process, a DNA sequence under control of regulatory regions, particularly the promoter sequence disclosed herein, is transcribed into an RNA molecule. An RNA molecule may either itself form an expression product and is then, for example, capable of interacting with another nucleic acid or protein. Alternatively, an RNA molecule may be an intermediate product when it is capable of being translated into a peptide or protein. A gene is said to encode an RNA molecule as expression product when the RNA as the end product of the expression of the gene is capable of interacting with another nucleic acid or protein. Examples of RNA expression products include inhibitory RNAs such as e.g. sense RNA, antisense RNA, hairpin RNA, ribozymes, miRNA or siRNA, mRNA, rRNA and tRNA. A gene is said to encode a protein or peptide as expression product when the end product of the expression of the gene is a protein or peptide.

Exemplary expression products of interest include proteins involved in cell wall synthesis and fiber formation as disclosed in WO2005/017157, in particular a gene encoding a β-1,3 glucan synthase protein, or in WO2006/136351, in particular an N-acetylglucosamine transferase which can be targeted to the membranes of the Golgi-apparatus, such as a N-acetylglucosamine transferase of the NodC type, or a chitin synthase and those described above in connection with suitable heterologous nucleic acids.

Within the scope of the present disclosure, use may also be made, in combination with the chimeric gene described above, of other regulatory sequences, which are located between said nucleic acid sequence comprising a promoter and said nucleic acid sequence comprising the coding sequence of the expression product. Non-limiting examples of such regulatory sequences include translation activators ("enhancers"), for instance the translation activator of the tobacco mosaic virus (TMV) described in Application WO 87/07644, or of the tobacco etch virus (TEV) described by Carrington & Freed 1990, J. Virol. 64: 1590-1597, or introns such as the *Arabidopsis* histone 3 intron (Chaubet et al., 1992).

Other suitable regulatory sequences include 5' UTRs. As used herein, a 5'UTR, also referred to as leader sequence, is a particular region of a messenger RNA (mRNA) located between the transcription start site and the start codon of the coding region. It is involved in mRNA stability and translation efficiency. For example, the 5' untranslated leader of a petunia chlorophyll a/b binding protein gene (cab22L) downstream of the 35S transcription start site can be utilized to augment steady-state levels of reporter gene expression (Harpster et al., 1988, Mol Gen Genet. 212(1):182-90). WO95/006742 describes the use of 5' non-translated leader sequences derived from genes coding for heat shock proteins to increase transgene expression.

Such UTRs are particularly useful if the nucleic acid sequence constituting the promoter of the present invention does not comprise the first 39 nucleotides 5' of the translation start (i.e. nucleotides 1398 to 1437 of SEQ ID NO: 1). In other words, such UTRs may advantageously be used if the promoter of the present invention does not reach further than to nucleotide 1398 or nucleotide 1394 of SEQ ID NO: 1. Preferably, in such cases the resulting promoter region is still capable of directing fiber-preferential or fiber-specific expression of the gene operably linked thereto.

The chimeric gene also comprises a transcription termination or polyadenylation sequence operable in a plant cell, particularly a cotton plant cell. As a transcription termination or polyadenylation sequence, use may be made of any corresponding sequence of bacterial origin, such as for example the nos terminator of *Agrobacterium tumefaciens*, of viral origin, such as for example the CaMV 35S terminator, or of plant origin, such as for example a histone terminator as described in published Patent Application EP 0 633 317 A1.

In one example of the chimeric gene described herein, said expression product of interest is a protein, a peptide or an RNA molecule, said RNA molecule capable of modulating the expression of a gene endogenous to said plant. In one example, said protein, peptide or RNA molecule is capable of modulating a fiber property. In another example, said protein, peptide or RNA molecule is involved in auxin biosynthesis.

The term "protein" as used herein describes a group of molecules consisting of more than 30 amino acids, whereas the term "peptide" describes molecules consisting of up to 30 amino acids. Proteins and peptides may further form dimers, trimers and higher oligomers, i.e. consisting of more than one (poly)peptide molecule. Protein or peptide molecules forming such dimers, trimers etc. may be identical or non-identical. The corresponding higher order structures are, consequently, termed homo- or heterodimers, homo- or heterotrimers etc. The terms "protein" and "peptide" also refer to naturally modified proteins or peptides wherein the modification is effected e.g. by glycosylation, acetylation, phosphorylation and the like. Such modifications are well known in the art.

Example proteins suitable as expression products include proteins involved in the modification of fiber properties, such as those mediating an increase in fiber length, an alteration in fiber strength or an alteration in the cell wall properties resulting, e.g. in an altered charge of said cell walls, an alteration in dyeability, decreased fuzz fiber production, an alteration in the fiber maturity ratio, a decrease in immature fiber content, or an increase in fiber uniformity and micronaire.

Said expression product of interest may also be an RNA molecule capable of modulating the expression of a gene endogenous to said cotton plant.

Examples of target genes suitable for RNA expression products in this connection include those involved in the modification of fiber properties, such as those mediating an increase in fiber length, an alteration in fiber strength or an alteration in the cell wall properties resulting, e.g. in an altered charge of said cell walls, an alteration in dyeability, decreased fuzz fiber production, an alteration in the fiber maturity ratio, a decrease in immature fiber content, or an increase in fiber uniformity and micronaire.

For the case of RNA molecules, it will be clear that whenever nucleic acid sequences of RNA molecules are defined by reference to nucleic acid sequences of corresponding DNA molecules, the thymine (T) in the nucleic acid sequence should be replaced by uracil (U). Whether reference is made to RNA or DNA molecules will be clear from the context of the application.

The term "capable of modulating the expression of a gene" relates to the action of an RNA molecule, such as an inhibitory RNA molecule as described herein, to influence the expression level of target genes in different ways. This can be effected e.g. by inhibiting the expression of a target gene by directly interacting with components driving said expression such as the gene itself or the transcribed mRNA which results in a decrease of expression, or by inhibiting another gene involved in activating the expression of a target gene thereby abolishing said activation, or inhibiting another gene involved in inhibiting the expression of a target gene which results in an increase of expression. The inhibition of a gene involved in inhibiting the expression of a target gene using inhibitory RNA may, on the contrary, result in an activation of expression of said target gene.

Inhibitory RNA molecules decrease the levels of mRNAs of their target proteins available for translation into said target protein. In this way, expression of proteins involved in unwanted responses to stress conditions can be inhibited. This can be achieved through well-established techniques including co-suppression (sense RNA suppression), antisense RNA, double-stranded RNA (dsRNA), siRNA or microRNA (miRNA).

An RNA molecule as expression product as disclosed herein comprises a part of a nucleic acid sequence encoding a target protein or a homologous sequence to down-regulate the expression of said target protein. Another example for an RNA molecule as expression product for use in down-regulating expression are antisense RNA molecules comprising a nucleic acid sequence complementary to at least a part of a nucleic acid sequence encoding a protein of interest or a homologous sequence. Here, down-regulation may be effected e.g. by introducing this antisense RNA or a chimeric DNA encoding such RNA molecule. In yet another example, expression of a protein of interest is down-regulated by introducing a double-stranded RNA molecule comprising a sense and an antisense RNA region corresponding to and respectively complementary to at least part of a gene sequence encoding said protein of interest, which sense and antisense RNA region are capable of forming a double stranded RNA region with each other. Such double-stranded RNA molecule may be encoded both by sense and antisense molecules as described above and by a single-stranded molecule being processed to form siRNA or miRNA.

In one example, expression of a target protein may be down-regulated by introducing a chimeric DNA construct which yields a sense RNA molecule capable of down-regulating expression by co-suppression. The transcribed DNA region will yield upon transcription a so-called sense RNA molecule capable of reducing the expression of a gene encoding a target protein in the target plant or plant cell in a transcriptional or post-transcriptional manner. The transcribed DNA region (and resulting RNA molecule) comprises at least 20 consecutive nucleotides having at least 95% sequence identity to the corresponding portion of the nucleic acid sequence encoding the target protein present in the plant cell or plant.

Alternatively, an expression product for down-regulating expression of a target protein is an antisense RNA molecule. Down-regulating or reducing the expression of a protein of interest in the target cotton plant or plant cell is again effected in a transcriptional or post-transcriptional manner. The transcribed DNA region (and resulting RNA molecule) comprises at least 20 consecutive nucleotides having at least 95% sequence identity to the complement of the corresponding portion of the nucleic acid sequence encoding said target protein present in the plant cell or plant.

However, the minimum nucleic acid sequence of the antisense or sense RNA region of about 20 nt (nucleotides) of the nucleic acid sequence encoding a target protein may be comprised within a larger RNA molecule, varying in size from 20 nt to a length equal to the size of the target gene. The mentioned antisense or sense nucleic acid regions may thus be from about 21 nt to about 5000 nt long, such as 21 nt, 40 nt, 50 nt, 100 nt, 200 nt, 300 nt, 500 nt, 1000 nt, 2000 nt or even about 5000 nt or larger in length. Moreover, it is not required for the purpose of the invention that the nucleic acid sequence of the used inhibitory RNA molecule or the encoding region of the transgene, is completely identical or complementary to the endogenous gene encoding the target protein the expression of which is targeted to be reduced in the plant cell. The longer the sequence, the less stringent the requirement for the overall sequence identity is. Thus, the sense or antisense regions may have an overall sequence identity of about 40% or 50% or 60% or 70% or 80% or 90% or 100% to the nucleic acid sequence of an endogenous gene or the complement thereof. However, as mentioned, antisense or sense regions should comprise a nucleic acid sequence of 20 consecutive nucleotides having about 95 to about 100% sequence identity to the nucleic acid sequence of the endogenous gene encoding the target gene. The stretch of about 95 to about 100% sequence identity may be about 50, 75 or 100 nt.

The efficiency of the above mentioned chimeric genes for antisense RNA or sense RNA-mediated gene expression level down-regulation may be further enhanced by inclusion of DNA elements which result in the expression of aberrant, non-polyadenylated inhibitory RNA molecules. One such DNA element suitable for that purpose is a DNA region encoding a self-splicing ribozyme. The efficiency may also be enhanced by providing the generated RNA molecules with nuclear localization or retention signals.

In addition, an expression product as described herein may be a nucleic acid sequence which yields a double-stranded RNA molecule capable of down-regulating expression of a gene encoding a target protein. Upon transcription of the DNA region the RNA is able to form dsRNA molecule through conventional base paring between a sense and antisense region, whereby the sense and antisense region are nucleic acid sequences as hereinbefore described. Expression products being dsRNA according to the invention may further comprise an intron, such as a heterologous intron, located e.g. in the spacer sequence between the sense and antisense RNA regions in accordance with the disclosure of WO 99/53050. To achieve the construction of such a transgene, use can be made of the vectors described in WO 02/059294 A1.

In an example, said RNA molecule comprises a first and second RNA region wherein 1. said first RNA region comprises a nucleic acid sequence of at least 19 consecutive nucleotides having at least about 94% sequence identity to the nucleic acid sequence of said endogenous gene; 2. said second RNA region comprises a nucleic acid sequence complementary to said 19 consecutive nucleotides of said first RNA region; 3. said first and second RNA region are capable of base-pairing to form a double stranded RNA molecule between at least said 19 consecutive nucleotides of said first and second region. In other examples, the same considerations apply as described above for sense and antisense RNA.

Another example expression product is a microRNA molecule (mirRNA, which may be processed from a pre-microRNA molecule) capable of guiding the cleavage of mRNA transcribed from the DNA encoding the target protein which is to be translated into said target protein. miRNA molecules may be conveniently introduced into plant cells through expression from a chimeric gene as described herein comprising a (second) nucleic acid sequence encoding as expression product of interest such miRNA, pre-miRNA or primary miRNA transcript.

miRNAs are small endogenous RNAs that regulate gene expression in plants, but also in other eukaryotes. As used herein, a "miRNA" is an RNA molecule of about 20 to 30 nucleotides (Siomi and Siomi, 2009) in length which can be loaded into a RISC complex and direct the cleavage of a target RNA molecule, wherein the target RNA molecule comprises a nucleic acid sequence essentially complementary to the nucleic acid sequence of the miRNA molecule. In example miRNAs, one or more of the following mismatches in the miRNA essentially complementary to the target RNA may occur:

A mismatch between the nucleotide at the 5' end of said miRNA and the corresponding nucleic acid sequence in the target RNA molecule;

A mismatch between any one of the nucleotides in position 1 to position 9 of said miRNA and the corresponding nucleic acid sequence in the target RNA molecule;

Three mismatches between any one of the nucleotides in position 12 to position 21 of said miRNA and the corresponding nucleic acid sequence in the target RNA molecule provided that there are no more than two consecutive mismatches;

No mismatch is allowed at positions 10 and 11 of the miRNA (all miRNA positions are indicated starting from the 5' end of the miRNA molecule).

As used herein, a "pre-miRNA" molecule is an RNA molecule of about 100 to about 200 nucleotides, preferably about 100 to about 130 nucleotides which can adopt a secondary structure comprising a dsRNA stem and a single stranded RNA loop and further comprising the nucleic acid sequence of the miRNA and its complement sequence of the miRNA* in the double-stranded RNA stem. Preferably, the miRNA and its complement are located about 10 to about 20 nucleotides from the free ends of the miRNA dsRNA stem. The length and sequence of the single stranded loop region are not critical and may vary considerably, e.g. between 30 and 50 nt in length. Preferably, the difference in free energy between unpaired and paired RNA structure is between −20 and −60 kcal/mole, for example around −40 kcal/mole. The complementarity between the miRNA and the miRNA* does not need to be perfect and about 1 to 3 bulges of unpaired nucleotides can be tolerated. The secondary structure adopted by an RNA molecule can be predicted by computer algorithms conventional in the art such as mFold, UNAFold and RNAFold. The particular strand of the dsRNA stem from the pre-miRNA which is released by DCL activity and loaded onto the RISC complex is determined by the degree of complementarity at the 5' end, whereby the strand which at its 5' end is the least involved in hydrogen bonding between the nucleotides of the different strands of the cleaved dsRNA stem is loaded onto the RISC complex and will determine the sequence specificity of the target RNA molecule degradation. However, if empirically the miRNA molecule from a particular synthetic pre-miRNA molecule is not functional because the "wrong" strand is loaded on the RISC complex, it will be immediately evident that this problem can be solved by exchanging the position of the miRNA molecule and its complement on the respective strands of the dsRNA stem of the pre-miRNA molecule. As is known in the art, binding between A and U involving two hydrogen bounds, or G and U involving two hydrogen bounds is less strong that between G and C involving three hydrogen bounds.

miRNA molecules may be comprised within their naturally occurring pre-miRNA molecules but they can also be introduced into existing pre-miRNA molecule scaffolds by exchanging the nucleic acid sequence of the miRNA molecule normally processed from such existing pre-miRNA molecule for the nucleic acid sequence of another miRNA of interest. The scaffold of the pre-miRNA can also be completely synthetic. Likewise, synthetic miRNA molecules may be comprised within, and processed from, existing pre-miRNA molecule scaffolds or synthetic pre-miRNA scaffolds.

Example expression products can also be ribozymes catalyzing either their own cleavage or the cleavage of other RNAs.

In one example of the chimeric gene disclosed herein modulating the expression is increasing the expression and said nucleic acid sequence encoding an expression product of interest encodes an RNA, which when transcribed yields an RNA molecule capable of increasing the expression of a gene endogenous to said cotton plant. Such genes could be positively correlated with fiber length, fiber strength or a desired alteration in the cell wall properties resulting, e.g. in an altered charge of said cell walls, an alteration in dyeability, decreased fuzz fiber production, an alteration in the fiber maturity ratio, a decrease in immature fiber content, or an increase in fiber uniformity and micronaire, or 2. yields an RNA molecule capable of decreasing the expression of a gene endogenous to said cotton plant, wherein said gene may be negatively correlated with fiber length, fiber strength or a desired alteration in the cell wall properties resulting, e.g. in an altered charge of said cell walls, an alteration in dyeability, decreased fuzz fiber production, an alteration in the fiber maturity ratio, a decrease in immature fiber content, or an increase in fiber uniformity and micronaire.

In another example of the chimeric gene described herein, said expression product is a reporter gene or a fiber-specific gene as described elsewhere in this application.

In one example of the chimeric gene described herein, said RNA molecule comprises a first and second RNA region wherein 1. said first RNA region comprises a nucleic acid sequence of at least 19 consecutive nucleotides having at least about 94% sequence identity to the nucleic acid sequence of said endogenous gene; 2. said second RNA region comprises a nucleic acid sequence complementary to said 19 consecutive nucleotides of said first RNA region; and 3. said first and second RNA region are capable of base-pairing to form a double stranded RNA molecule between at least said 19 consecutive nucleotides of said first and second region.

Vectors

In one embodiment, the present invention relates to a vector comprising the nucleic acid or the chimeric gene described herein.

A "vector" refers to any nucleic acid-based agent capable of carrying and transferring genetic information such as a plasmid, cosmid, virus, autonomously replicating sequence, phage, or linear single-stranded, circular single-stranded, linear double-stranded, or circular double-stranded DNA or RNA nucleic acid sequence. The recombinant vector may be derived from any source and is capable of genomic integration or autonomous replication. Thus, the chimeric gene described above may be provided in a recombinant vector. A recombinant vector typically comprises, in a 5' to 3' orientation: a promoter to direct the transcription of a nucleic acid sequence and a nucleic acid sequence to be transcribed. These elements correspond to the chimeric gene disclosed herein to be introduced. The recombinant vector may further comprise a 3' transcriptional terminator, a 3' polyadenylation signal, other untranslated nucleic acid sequences, transit and targeting nucleic acid sequences, selectable markers, enhancers, and operators, as desired. The wording "5' UTR" refers to the untranslated region of DNA upstream, or 5' of the coding region of a gene and "3' UTR" refers to the untranslated region of DNA downstream, or 3' of the coding region of a gene. Means for preparing recombinant vectors are well known in the art. Methods for making recombinant vectors particularly suited to plant transformation are described in U.S. Pat. No. 4,971,908, U.S. Pat. No. 4,940,835, U.S. Pat. No. 4,769,061 and U.S. Pat. No. 4,757,011. The vector described herein may be an expression vector. Typical vectors useful for expression of nucleic acids in higher plants are well known in the art and include vectors derived from the tumor-inducing (Ti) plasmid of *Agrobacterium tumefaciens*, e.g. those disclosed in Cornelissen and Vandewiele (1989), Lindbo (2007) or Wagner et al (2004).

Plant Cells and Plants

The present invention is also directed to transgenic plant cells and transgenic plants which comprise a nucleic acid sequence as described above, i.e. the promoter sequence disclosed herein, operably linked to a heterologous nucleic acid sequence encoding an expression product of interest. Alternatively, said transgenic plant cells or plants comprise the chimeric gene or the vector disclosed herein. Example promoter sequences and expression products of interest and other regulatory elements, are described above.

A transgenic plant cell or plant may be produced by introducing the nucleic acid sequence(s) as described above into plants or plant cells. "Introducing" in connection with the present application relates to the placing of genetic information in a plant cell or plant by artificial means. This can be effected by any method known in the art for introducing RNA or DNA into plant cells, protoplasts, calli, roots, tubers, seeds, stems, leaves, seedlings, embryos, pollen and microspores, other plant tissues, or whole plants. More particularly, "introducing" means stably integrating into the plant's genome.

Plants containing at least one transformed nucleic acid sequence are referred to as "transgenic plants". Transgenic and recombinant refer to a host organism such as a plant into which a heterologous nucleic acid molecule (e.g. the nucleic acid sequence, the chimeric gene or the vector as described herein) has been introduced. The nucleic acid can be stably integrated into the genome of the plant. Specific methods for introduction are described in connection with the methods disclosed herein.

The plant cell may be derived from any fiber-producing plant, such as *Gossypium* (cotton).

"Cotton" or "cotton plant" as used herein can be any variety useful for growing cotton. The most commonly used cotton varieties are *Gossypium barbadense, G. hirsutum, G. arboreum* and *G. herbaceum*. Further varieties include *G. africanum* and *G. raimondii*. Also included are progeny from crosses of any of the above species with other species or crosses between such species.

A cotton plant cell may be any cell comprising essentially the genetic information necessary to define a cotton plant, which may, apart from the chimeric gene disclosed herein, be supplemented by one or more further transgenes. Cells may be derived from the various organs and/or tissues forming a cotton plant, including but not limited to fruits, seeds, embryos, reproductive tissue, meristematic regions, callus tissue, leaves, roots, shoots, flowers, vascular tissue, gametophytes, sporophytes, pollen, and microspores.

The present application also discloses a transgenic plant consisting of the transgenic cotton plant cells described hereinabove, or comprising the chimeric gene or the vector described herein stably integrated in the plant genome. This may be effected by transformation protocols described elsewhere in this application.

In another embodiment, the present invention relates to a seed generated from a transgenic plant described herein, wherein said seed comprises the chimeric gene described herein.

Seed is formed by an embryonic plant enclosed together with stored nutrients by a seed coat. It is the product of the ripened ovule of gymnosperm and angiosperm plants, to the latter of which cotton belongs, which occurs after fertilization and to a certain extent growth within the mother plant.

Further disclosed herein are cotton fibers and cotton seed oil obtainable or obtained from the plants disclosed herein. Cotton fibers disclosed herein can be distinguished from other fibers by applying the detection method disclosed in WO2010/015423 and checking for the presence of the nucleic acid of (a) or chimeric gene of (b) in the fibers. Accordingly, the nucleic acid of (a) may also be used for tracking cell walls, in particular cotton fibers according to the invention.

Also disclosed herein are yarn and textiles made from the fibers disclosed herein as well as foodstuff and feed comprising or made of the cotton seed oil disclosed herein. A method to obtain cotton seed oil comprising harvesting cotton seeds from the cotton plant disclosed herein and extracting said oil from said seeds is also disclosed. Further, a method to produce cotton fibers comprising growing the cotton plant disclosed herein and harvesting cotton from said cotton plants is also disclosed.

Methods and Uses

The present invention furthermore relates to a method of producing a transgenic plant (a) providing a chimeric gene described herein or a vector described herein; and (b) introducing said chimeric gene or vector in a plant.

A number of methods are available to introduce DNA into plant cells or plants, either by transformation or introgression. *Agrobacterium*-mediated transformation of cotton has been described e.g. in U.S. Pat. Nos. 5,004,863, 6,483,013 and WO 2000/71733.

Plants may also be transformed by particle bombardment: Particles of gold or tungsten are coated with DNA and then shot into young plant cells or plant embryos. This method also allows transformation of plant plastids. Cotton transformation by particle bombardment is reported e.g. in WO 92/15675.

Viral transformation (transduction) may be used for transient or stable expression of a gene, depending on the nature of the virus genome. The desired genetic material is packaged into a suitable plant virus and the modified virus is allowed to infect the plant. The progeny of the infected plants is virus free and also free of the inserted gene. Suitable methods for viral transformation are described or further detailed e.g. in WO 90/12107, WO 03/052108 or WO 2005/098004.

"Introgressing" means the integration of a gene in a plant's genome by natural means, i.e. by crossing a plant comprising the chimeric gene described herein with a plant not comprising said chimeric gene. The offspring can be selected for those comprising the chimeric gene.

Further transformation and introgression protocols can also be found in U.S. Pat. No. 7,172,881.

The chimeric gene may be introduced, e.g. by transformation, in cotton plants from which embryogenic callus can be derived, such as Coker 312, Coker310, GSC25110, FIBERMAX 819, Siokra 1-3, T25, GSA75, Acala SJ2, Acala SJ4, Acala SJ5, Acala SJ-C1, Acala B1644, Acala B1654-26, Acala B1654-43, Acala B3991, Acala GC356, Acala GC510, Acala GAM1, Acala C1, Acala Royale, Acala Maxxa, Acala Prema, Acala B638, Acala B1810, Acala B2724, Acala B4894, Acala B5002, non Acala "picker" Siokra, "stripper" variety FC2017, Coker 315, STONEVILLE 506, STONEVILLE 825, DP50, DP61, DP90, DP77, DES119, McN235, HBX87, HBX191, HBX107, FC 3027, CHEMBRED A1, CHEMBRED A2, CHEMBRED A3, CHEMBRED A4, CHEMBRED B1, CHEMBRED B2, CHEMBRED B3, CHEMBRED C1, CHEMBRED C2, CHEMBRED C3, CHEMBRED C4, PAYMASTER 145, HS26, HS46, SICALA, PIMA S6 ORO BLANCO PIMA, FIBERMAX FM5013, FIBERMAX FM5015, FIBERMAX FM5017, FIBERMAX FM989, FIBERMAX FM832, FIBERMAX FM966, FIBERMAX FM958, FIBERMAX FM989, FIBERMAX FM958, FIBERMAX FM832, FIBERMAX FM991, FIBERMAX FM819, FIBERMAX FM800, FIBERMAX FM960, FIBERMAX FM966, FIBERMAX FM981, FIBERMAX FM5035, FIBERMAX FM5044, FIBERMAX FM5045, FIBERMAX FM5013, FIBERMAX FM5015, FIBERMAX FM5017 or FIBERMAX FM5024 and plants with genotypes derived thereof.

In a further aspect, the present application discloses a method of growing cotton comprising (a1) providing the transgenic plant described herein or produced by the method described herein; or (a2) introducing a chimeric gene according described herein or a vector described herein in a plant; (b) growing the plant of (a1) or (a2); and (c) harvesting cotton produced by said plant.

"Growing" relates to creating the environment for plants to grow, multiply and/or age. Suitable growing conditions for specific plants are well-known in the art.

In another aspect, the present application discloses to a method of producing a seed comprising the chimeric gene disclosed herein comprising (a) growing a transgenic plant comprising the chimeric gene described herein or the vector described herein, a transgenic plant described herein or a transgenic plant obtained by the method described herein, wherein said transgenic plant produces said seed and said chimeric gene is comprised in said seed, and (b) isolating said seed from said transgenic plant.

In one example of the method of producing a transgenic plant or the method of producing a seed, the plant is a cotton plant as described elsewhere in this application.

In another aspect, the present application discloses to a method of effecting fiber-preferential expression of a product in cotton comprising introducing the chimeric gene disclosed herein or the vector disclosed herein into the genome of a cotton plant; or providing the transgenic plant disclosed herein.

In a further aspect, the present application discloses a method of altering fiber properties in a cotton plant comprising introducing the chimeric gene disclosed herein or the vector disclosed herein into the genome of a cotton plant; or providing the transgenic plant disclosed herein.

In one example, the method further comprises growing said plant until seed are generated.

In another example based on the above further step, the method is for increasing cotton yield from a cotton plant and further comprises harvesting the cotton produced by said cotton plant. In other words disclosed herein is a method for increasing cotton yield from a cotton plant comprising introducing the chimeric gene disclosed herein or the vector disclosed herein into the genome of a cotton plant; or providing the transgenic plant disclosed herein; growing said plant until seed are generated; and harvesting the cotton produced by said cotton plant.

The term "increasing the yield" in connection with the present application relates to an increase in the output of cotton fibers which can be achieved e.g. by increasing the number of fibers produced on a cotton seed, the length of the fibers or the strength of the fibers. Genes and expression products thereof involved in conferring these properties have been described above.

Example features for a modification of fiber properties are fiber length, fiber strength, an alteration in the cell wall properties resulting, e.g. in an altered charge of cell walls, dyeability, decreased fuzz fiber production or content, fiber maturity ratio, immature fiber content, fiber uniformity and micronaire.

In another aspect, the present application discloses the use of the chimeric gene disclosed herein, the vector disclosed herein or the transgenic plant or plant cell disclosed herein for fiber-preferential expression of a product in cotton, for altering fiber properties in cotton or for increasing cotton yield. The definitions and further examples described above for other aspects disclosed herein equally apply to the present aspect.

The transformed plant cells and plants described herein such as those obtained by the methods described herein may be further used in breeding procedures well known in the art, such as crossing, selfing, and backcrossing. Breeding programs may involve crossing to generate an F1 (first filial) generation, followed by several generations of selfing (generating F2, F3, etc.). The breeding program may also involve backcrossing (BC) steps, whereby the offspring is backcrossed to one of the parental lines, termed the recurrent parent.

Accordingly, also disclosed herein is a method for producing plants comprising the chimeric gene disclosed herein comprising the step of crossing the cotton plant disclosed herein with another plant or with itself and selecting for offspring comprising said chimeric gene.

The transgenic plant cells and plants obtained by the methods disclosed herein may also be further used in subsequent transformation procedures, e.g. to introduce a further chimeric gene.

The cotton plants or seed comprising the chimeric gene disclosed herein or obtained by the methods disclosed herein may further be treated with cotton herbicides such as Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; cotton insecticides such as Acephate, Aldicarb, Chlorpyrifos, Cypermethrin, Deltamethrin, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl] (2,2-difluorethyl)amino]furan-2(5H)-on, Thiodicarb, Avermectin, Flonicamid, Pyridalyl, Spiromesifen, Sulfoxaflor; and cotton fungicides such as Azoxystrobin, Bixafen, Boscalid, Carbendazim, Chlorothalonil, Copper, Cyproconazole, Difenoconazole, Dimoxystrobin, Epoxiconazole, Fenamidone, Fluazinam, Fluopyram, Fluoxastrobin, Fluxapyroxad, Iprodione, Isopyrazam, Isotianil, Mancozeb, Maneb, Metominostrobin, Penthiopyrad, Picoxystrobin, Propineb, Prothioconazole, Pyraclostrobin, Quintozene, Tebuconazole, Tetraconazole, Thiophanate-methyl, Trifloxystrobin. For a treatment with cotton herbicides, said cotton plants or seed preferably further comprise a trait conferring a respective herbicide tolerance or are naturally tolerant to a herbicide.

The figures show:

FIG. 1: Relative expression of Fb8-Like genes in different tissues compared to 35 dpa fibers using the cotton ubiquitin gene as a reference. Primers were to a consensus of a number of very similar Fb8-like ESTs. Values are the average of four technical replicates.

FIG. 2: Alignment of deduced protein sequences of the Fb8-like protein encoded by BAC150F2 (SEQ ID NO:13) compared to the cDNA encoded protein from cFB8-like#1 (SEQ ID NO:14) aligned using ClustalW. Identical amino acids are boxed in black and similar amino acids in gray.

Figure 3:
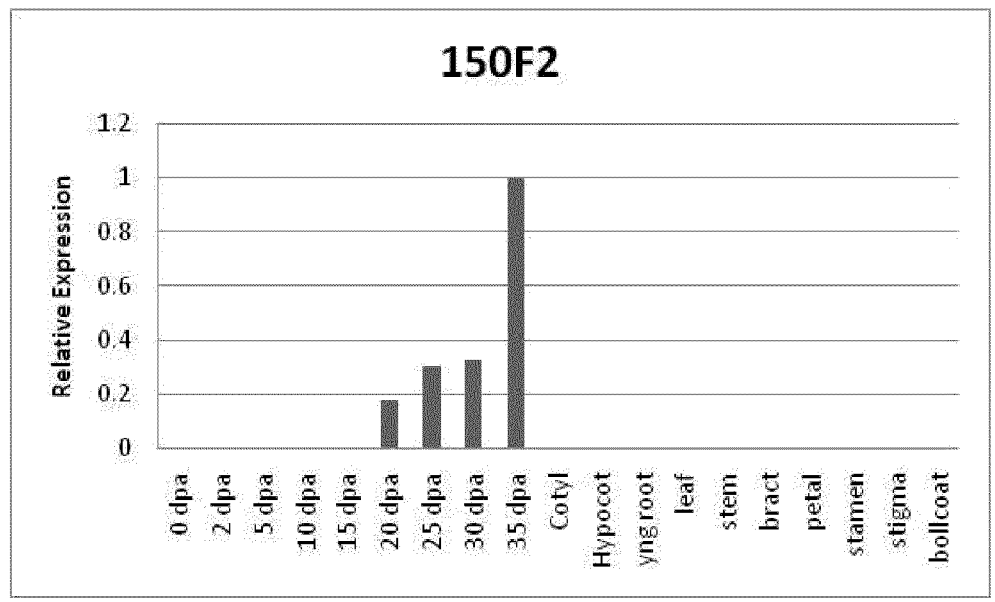

FIG. 3: Relative expression of the specific Fb8-Like gene encoded by BAC150F2 in different tissues compared to 35 dpa fibers using the cotton ubiquitin gene as a reference. Values are the average of four technical replicates.

Figure 4:
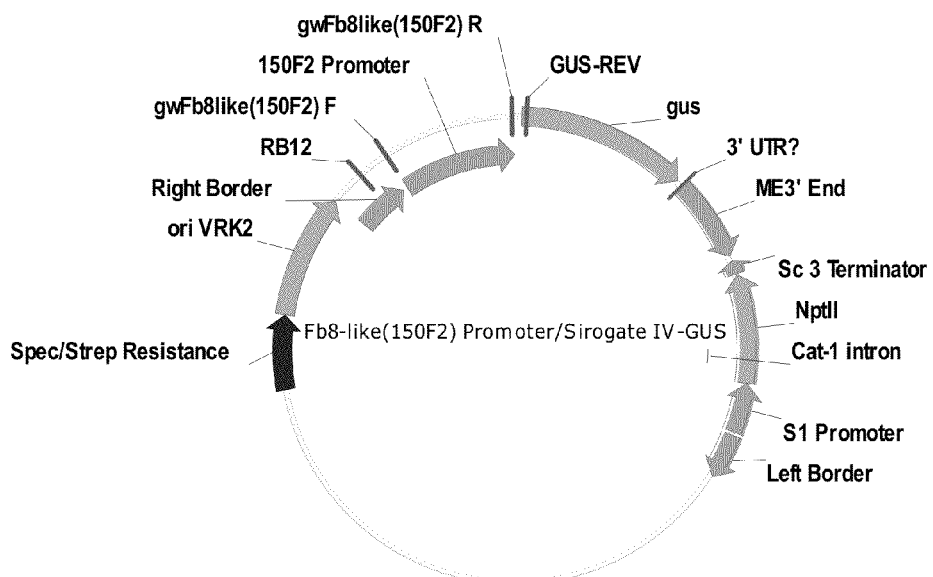

FIG. 4: A Schematic of the Fb8-like(150F2) promoter GUS construct transformed into cotton; B sequence of the vector including the Fb8-like(150F2) promoter GUS construct (SEQ ID NO:15).

Figure 5:
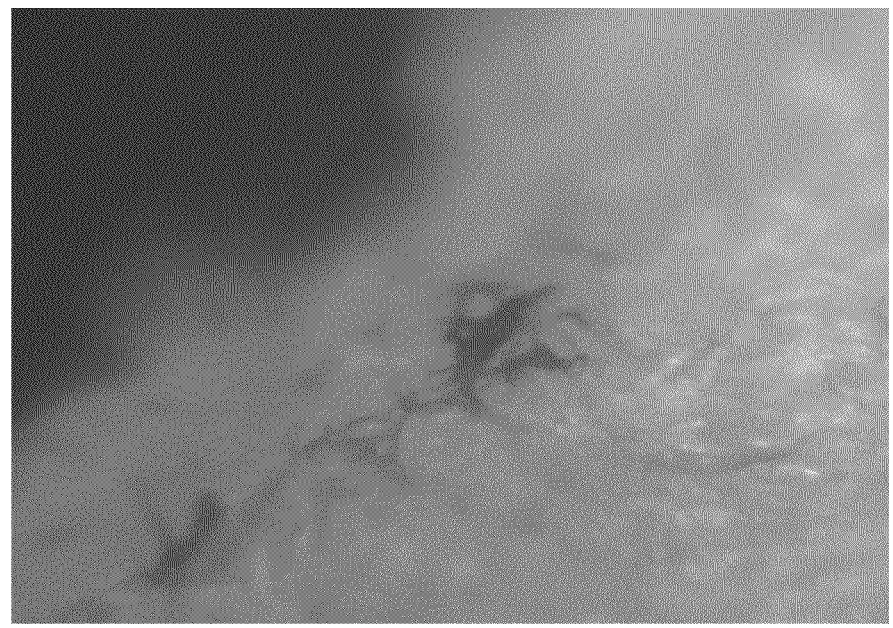

FIG. 5: 29dpa-fiber GUS staining of Fb8-like (150F2)-GUS bombarded cotton ovule cultures.

Figure 6:
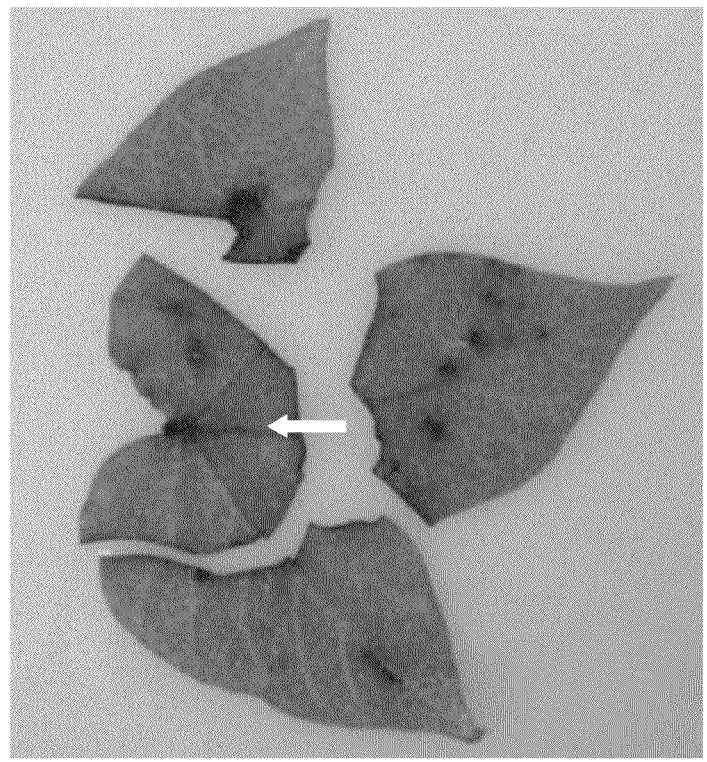

FIG. 6: GUS staining around the cut edges of fully expanded leaves of line T424-42, but not along edges that haven't been cut. Areas of GUS staining in the middle of the leaves were areas that had been damaged prior to staining probably by thrips (white arrow).

The examples illustrate the invention

EXAMPLE 1

Identification of Candidate Genes Expressed Preferentially in Fibers

A list of about 450 potential fiber expressed genes was generated from an analysis of the literature and public microarray data and this was narrowed down through a process of examining the frequency of occurrence of ESTs homologous to those genes in public databases (as a surrogate of transcript abundance) and then followed up with quantitative RT-PCR across a range of tissue types and fiber ages. It was decided to particularly look at the gene F203F9 (DR176749, Fb8-like). This is a gene originally identified by Liu et al. (2006) by suppression-subtractive hybridisation from the fibers of G. hirsutum cultivar TM-1. Liu et al., 2006 noted that clone F203F9 (lodged as Genbank accession DR176749) was predominantly expressed in 20 dpa fibers, but not expressed in 10 dpa fibers. In that publication the EST was annotated as very similar to the G. barbadense cDNA Fb8-like (AF531368), but is also closely related to the G. barbadense FbLate-2 (U34401) cDNA, both members of a multigene family in cotton.

A blastN search of the Genbank cotton ESTs with DR176749 identified several very similar ESTs, including AF531368, confirming that this gene was a member of a multigene family. DR176749 was identical over most of its length to the longer EST sequence of AF531368 so this was used to design primers (Fb8-like_F: 5'-attcttttctttctatttggt-taaccat-3' (SEQ ID NO: 2) and Fb8-like_R: 5'-tagtgctcgagccagactga-3' (SEQ ID NO: 3)) that flanked the coding region of AF531368 Fb8-like EST to amplify the gene(s) from Upland cotton fiber cDNA and genomic DNA to examine the diversity within this gene family.

Both cDNA (from a mix of 10 and 20 dpa Coker315 fiber mRNA) and genomic FB8-like clones (from Coker315 DNA) were cloned and sequenced and these varied in both length and sequence, confirming the multigenic nature of this family of Fb8-like genes. Three similar but different length clones, for example, were recovered from fiber cDNA with clone cFB8-like #1 being the closest in identity to AF531368, the *G. barbadense* FB8-like gene.

This cDNA encoded a predicted protein of 276 amino acids considerably longer than the 165 amino acid residues of the *G. barbadense* Fb8-like protein but very similar in sequence.

The protein has no recognized conserved domains (as confirmed by using the prediction platform provided on the world wide web at ncbi.nlm.nih.gov/Structure/cdd/wrpsb.cgi), but has a predicted signal peptide for secretion (as confirmed using the prediction platform provided on the world wide web at cbs.dtu.dk/services/SignalP/) and has an interesting repeat sequence structure of three glutamate-lysine rich domains as predicted by the RADAR website (on the world wide web at ebi.ac.uk/Tools/Radar/). The *G. barbadense* FB8-like protein has only the first of these three repeats.

Q-PCR primers were designed to near the C-terminal end of a consensus FB8-like sequence and used to profile the relative expression of Fb8-like genes in different tissues of the *G. hirsutum* cultivar Coker 315 using the ubiquitin gene as a reference. RNA preparation was carried out according to Wan and Wilkins (1994) with up to 2 g ground fibers or other tissues. All RNA preparations were DNAse treated and purified by organic extraction. Real time PCR experiments used 5 µg of total RNA for the production of cDNA according to the manufacturer's recommendations (Superscript II, BRL Life Technologies, Gaithersburg, Md., USA) and were primed with 0.5 µg of oligo-dT (dT18).

The primers used were designed with Primer 3 (on the world wide web at frodo.wi.mit.edu./cgi-bin/primer3/primer3_www.cgi) and were QFb8like_F: 5'-gagtgccaagagt-cacacga-3' (SEQ ID NO:4) and QFb8like_R: 5'-ttggatcccac-ccttaaaca-3' (SEQ ID NO: 5) that amplify a product of 113 bp. The primers for the cotton Ubiquitin gene were UbiQ_F: 5'-aatccactttgcacctggtc-3' (SEQ ID NO:6) and UbiQ_R: 5'-ctagtggccagctcacatca-3' (SEQ ID NO: 7) that amplify a product of 131 bp (Al Ghazi et al., 2009). Quantitative Real-time PCR experiments were carried out in an Applied Biosystems 7900HT Fast Real-time PCR system (CA.USA) according to the following procedure. 15 µL of a master mix consisting of 10 µl of 2×SYBR Green JumpStart Taq Ready Mix (Sigma), 0.5 µL of each 20 µM forward and reverse oligonucleotides corresponding to the given target gene and 4 µL of PCR grade water were pipetted into 96 well plates. The templates (5 µL of a 1/500 dilution of the cDNA reaction) were then added to the master mixes and transferred to the thermal cycler. Cycling conditions were 5 min of denaturation at 95° C. followed by 40 cycles of 95° C. denaturation for 15 seconds, 60° C. annealing for 15 seconds and 72° C. elongation for 20 seconds. Following amplification, a dissociation stage was carried out to detect any complex products. Data analysis was performed with RQmanager V1.2 software (Applied Biosystems) and relative transcript abundance compared to 35 dpa fibers determined using the cotton ubiquitin gene as a reference gene to correct for cDNA input using the ΔΔCt method.

According to the Q-PCR data (FIG. 1), the Fb8-Like family is most highly expressed in the cell wall thickening stage of fiber development (from 20 through to 35 dpa), although highest in about 35 dpa fibers, with little or no expression elsewhere.

EXAMPLE 2

Isolation of an Fb8-Like Promoter

The insert from the cFB8-like#1 cDNA clone was excised, gel purified and used as a probe to screen a large insert BAC library from *G. hirsutum* cv Acala Maxxa (GH_MBb, Clemson Genomics Institute) according to the suppliers recommended protocol (http://www.genome.clemson.edu/resources/protocols). Several strong hybridising BACs were obtained, DNA prepared and grouped by restriction pattern type using Southern blotting. Sequencing with primers in the coding region of the clones with unique restriction patterns identified the clone BAC150F2. BAC150F2 encoded a related but slightly smaller protein (FIG. 2).

The expression pattern of the Fb8-like gene encoded by BAC150F2 was confirmed with primers specific to this gene using Q-PCR. The primers used were 150F2_F 5'-tggctcat-agcattcgtcac-3' (SEQ ID NO: 8) and 150F2_R 5'-ccaattgtgg-gagctctgat-3' (SEQ ID NO: 9) from near the N-terminal end of the coding region and the cotton ubiquitin gene was used as the reference as indicated previously. The forward primer has 3 mismatches with the gene encoded by the BAC8K12 and the reverse primer 1 mismatch. The expression pattern of the 150F2 encoded gene (FIG. 3) was essentially the same as that observed using more generic FB8-like primers and looked to be fiber-preferential.

Sequencing upstream into the promoter and down into the coding region was carried out in a stepwise manner from BAC DNA. The encoded gene did not appear to contain an intron and encoded a protein of 249 amino acids. The sequence of the promoter and gene for BAC150F2 is shown in the following SEQ ID NO: 10 (coding region in italics; the promoter region used for the reporter expression construct is underlined. Regions contained within the gateway primers used to amplify the promoter from BAC DNA are indicated in bold):

```
agtccctaag ttcaaaacta taaattttca ctttagaaat taatcatttt tcacatctaa   60
gcatcaaatt taaccaaatg acacaaattt catgattagt tagatcaagc ttttgagtct  120
tcaaaaacat aaaaattaca aaaaaaaaac aaacttaaaa tcatttatca atttgaacaa  180
caaagcttgg ccgaatgcta agagcttaaa aatggcttct tttgtttctt tttgttgcaa  240
acggtggaga gaagagggaa atgaagattg accatatttt tttattatgt tttaacatat  300
aatattaata atttaatcat aattatactt tggtgaatgt gacagtgggg agatacgtaa  360
agtatataac attatacttt ttgcaagcag ttggctggtc tacccaagag tgatcaaagt  420
```

```
ttgagctgcc ttcaatgagc caattttttgc ccataatgga taaaggcaat ttgtttagtt    480
caactgctca cagaataatg ttaaaatgaa attaaaataa ggtggcctgg tcacacacac    540
aaaaaaaaac taatgttggt tggttgaatt ttatattacg gaatgtaata ttatattta     600 aaataaaatt atgttattta gattcttaat attttgagca ttccatacta taatttcgta    660
tacataatat taaaatatag taatataaag tgtaattaac tttaaattac aagcataata    720
ttaaattttg aatcaattaa ttttttatttc tattattta attaatttag tctattttt     780 caaaataaaa tttaaatcta aataaaaata attttccctt aatgttgaaa caactcatgt    840
tatacttcaa aattataagt attatattta ccttgatgat ttatttatta gtatattaat    900
tctgattata attatggtgg gatacaatcg ctttccacta aatattttaa ctatgattta    960
taaatttatt tcaacatcgt atatttactt attaatacat aatttatcat aattttatgg   1020
aaattgagac caagaaacat taagagaaca aattctataa caaagacaat ttagaaaaaa   1080
atgtactttt aggtaatttt aagtactctt aaccaaacac aaaaattcaa atcaaatgaa   1140
ctaaataaga taatataaca tacggaacat cttacttgta atcttacatt cccataattt   1200
tattatgaaa aataatctta tattactcga actaaatgtt gtcacaaatt attatctaaa   1260
taaagaaaaa cacttaattt ttataacatt ttttcatata tttgaaagat tatattttgt   1320
atatttacgt aaaaatattt gacatagatt gagcaccttc ttaacataat cccaccataa   1380
gtcaagtatg tagatgagaa attggtacaa acaacgtggg gccaaatccc accaaaccat   1440
ctctcattct ctcctataaa aggcttgcta cacatagaca acaatccaca cacaaataca   1500
cgttcttttc tttctatttg attaaccatg gctcatagca ttcgtcaccc tttcttcctt   1560
ttccaacttt tactcataag tgtctcacta gtgaccggta gccacactgt ttcggcagcg   1620
gctcgacgtt tattcgagac acaagcaacc tcatcagagc tcccacaatt ggcttcaaaa   1680
tacgaaaagc acgaagagtc tgaatacgaa aagccagaat acaaacagcc aaagtatcac   1740
gaagagtact caaaacttga gaagcctgaa atgcaaaagg aggaaaaaca aaaccctgc    1800 aaacagcatg aagagtacca cgagtcacac gaatcaaagg agcaaaaaga gtacgagaaa   1860
gaaaatctcg agttccccaa atgggaaaag cctaaagagc acgagaaaca cgaagtcgaa   1920
tatccgaaaa tacccgagta caaggtaaaa caagatgagg gcaaggaaca taaacatgaa   1980
gagtaccacg aatcacgcga atcgaaagag cacgaagagt acgagaaaga aaaacccgag   2040
ttccctaaat tggaaaagcc taaagagcac gagaaacacg aagtcgaata tccggaaata   2100
cccgaataca agaaaaagca agatgagggt aacgaacata acatgagtt cccaaagcat    2160 gaaaaagaag aggagaagaa acctgagaaa aaggcagagt accttgagtg ggctaaaatg   2220
cctgaatggt cgaagtccat gtttactcag cctggctcgg ccactaagcc ttgaatcata   2280
tgacactggt gcatgtgcca tcatcatgca gtaatttcat ggtatatcgt aatatatagt   2340
taataaaaaa gatggtgatt gggaaatgtg tgtgtgcatt cctccatgca ctaatggtga   2400
atctctttgc atacatagaa attctaaatg gttatagttt atgttatagt gtatgttgta   2460
gtgaaattaa ttttaaatgt tgtatctaat gttaacatca cttggcttga tttatgttat   2520
gttatgtatt ttactttaat gatattgcat gtattgttaa tttaacattg cttgatcatt   2580
atactcttct actattaatt ataaatggca ctgttttgtt taaacttttt acaagttaag   2640
acatgtataa atatatgaca atataattac aagttttagt tcaatgttag ctatcttagt   2700
atgttattga tgatcttaat tacatttaaa caaattcca                          2739
```

EXAMPLE 3

Production of an Expression Construct Comprising pFB8-Like Operably Linked to GUS A 1437 bp fragment of the promoter upstream from the ATG codon was amplified from BAC DNA of BAC150F2 using the gateway primers gwFb8-likePro (150F2)_F 5'-ggg-gacaagtttgtacaaaaaagcaggctcatgattagttagatcaagcttttgagt (SEQ ID NO: 11)-3' and gwFb8-likePro (150F2)_R 5'-ggg-gaccactttgtacaagaaagctgggtggttaatcaaatagaaga aaagaacgt-3' (SEQ ID NO: 12) (gene-specific sequences are in bold) containing the attB1 and attB2 recombination sites for in vitro recombination using the Gateway cloning system (Invitrogen). PCR amplification from BAC DNA followed by PEG cleanup was according to the manufacturer's instructions and in vitro recombination using the BP reaction with the intermediate vector pDONR201 (Invitrogen) and transformation into DH5alpha cells resulted in the production of pDONR/gwFb8-like (150F2). The intermediate vector was sequenced with pDONR-F and pDONR-R primers (Invitrogen) and then recombined into a GUS reporter gene destination vector using the LR reaction as recommended. This vector contains the left and right borders of the T-DNA, a promoterless GUS gene downstream of an attR gateway recombination cassette, a terminator from the *Flavaria bidentis* malic enzyme and a plant expressible kanamycin resistance gene with a promoter from the segment 1 sub-genomic RNA and terminator of segment 3 of the sub-clover stunt virus as described in Schünmann et al., (2003). The resultant plasmid pFb8-like (150F2)-GUS (FIG. 4) was sequenced with a primer in the GUS reporter gene to confirm the correct recombination of the promoter and then transferred to *Agrobacterium* strain AGL1 (Lazo et al., 1991) by electroporation.

The sequence of the promoter in 5'-3' direction corresponds to SEQ ID NO: 1

```
catgattagt tagatcaagc ttttgagtct tcaaaaacat aaaaattaca aaaaaaaaac    60
aaacttaaaa tcatttatca atttgaacaa caaagcttgg ccgaatgcta agagcttaaa   120
aatggcttct tttgtttctt tttgttgcaa acggtggaga gaagagggaa atgaagattg   180
accatatttt tttattatgt tttaacatat aatattaata atttaatcat aattatactt   240
tggtgaatgt gacagtgggg agatacgtaa agtatataac attatacttt ttgcaagcag   300
ttggctggtc tacccaagag tgatcaaagt ttgagctgcc ttcaatgagc caattttttgc   360
ccataatgga taaaggcaat ttgtttagtt caactgctca cagaataatg ttaaaatgaa   420
attaaaataa ggtggcctgg tcacacacac aaaaaaaaac taatgttggt tggttgaatt   480
ttatattacg gaatgtaata ttatatttta aaataaaatt atgttattta gattcttaat   540
attttgagca ttccatacta taatttcgta tacataatat taaaatatag taatataaag   600
tgtaattaac tttaaattac aagcataata ttaaatttg aatcaattaa tttttatttc   660
tattatttta attaatttag tctatttttt caaaataaaa tttaaatcta aataaaaata   720
attttccctt aatgttgaaa caactcatgt tatacttcaa aattataagt attatattta   780
ccttgatgat ttatttatta gtatattaat tctgattata attatggtgg gatacaatcg   840
ctttccacta aatatttaa ctatgattta taaatttatt tcaacatcgt atatttactt    900
attaatacat aatttatcat aatttttatgg aaattgagac caagaaacat taagagaaca   960
aattctataa caaagacaat ttagaaaaaa atgtacttt aggtaatttt aagtactctt   1020
aaccaaacac aaaaattcaa atcaaatgaa ctaaataaga taatataaca tacggaacat  1080
cttacttgta atcttacatt cccataattt tattatgaaa aataatctta tattactcga  1140
actaaatgtt gtcacaaatt attatctaaa taaagaaaaa cacttaatt ttataacatt   1200
ttttcatata tttgaaagat tatattttgt atatttacgt aaaaatattt gacatagatt  1260
gagcaccttc ttaacataat cccaccataa gtcaagtatg tagatgagaa attggtacaa  1320
acaacgtggg gccaaatccc accaaaccat ctctcattct ctcctataaa aggcttgcta  1380
cacatagaca acaatccaca cacaaataca cgttctttc tttctatttg attaacc      1437
```

EXAMPLE 4

Expression of a Construct Comprising pFb8-Like Operably Linked to GUS

Functionality of the promoter was tested by bombardment of pFb8-like (150F2)-GUS vector into cultured cotton ovules and staining for GUS enzyme activity (Jefferson et al., 1987). Gus activity was observed in 16 dpa and 29 dpa fibers (see Table 1 and FIG. 5).

TABLE 1 number of GUS spots/number of ovules analyzed.
The Fb8-like(150F2) promoter was able to drive
GUS expression between 16 dpa and 29 dpa.

| promoter | 16 dpa | 29 dpa |
| --- | --- | --- |
| 35S | 1/20 | not tested |
| Fb8-like(150F2) | 2/35 | 1/28 |

Cotton transformation with the *Agrobacterium* strain carrying the pFb8-like (150F2)-GUS vector was carried out essentially as described in Murray et al., (1999) using the seedling cotyledon segments of cotton cultivar Coker315-11 (a selection from the regenerable Coker 315 cultivar) and selection for resistance to kanamycin sulphate.

A total of 24 primary transformants were generated representing 14 independent transformation events. Plants were transferred to soil and allowed to flower. Flowers were tagged at anthesis and both 10 and 20 dpa bolls collected and whole seeds with fibers stained for GUS enzyme using X-gluc histochemical stains as described by Jefferson et al., 1987. Immature leaves, petiole segments, roots and stem sections from both young and older branches were also stained for GUS. Staining patterns for three different independent lines are summarized in Table 2.

TABLE 2

| Transformant line | Leaf | Petiole | Stem | Root | 10 dpa fiber | 20 dpa fiber |
| --- | --- | --- | --- | --- | --- | --- |
| T424-3 | + Staining in glandular trichomes and wounded areas of leaves | + Staining in some glandular trichomes | + Weak staining in pith and xylem | − | +++ | +++ |
| T424-42 | + Staining in glandular trichomes and wounded areas of leaves | + Staining in some glandular trichomes | + Weak staining in pith and xylem | − | +++ | +++ |
| T424-77 | + Staining in glandular trichomes and wounded areas of leaves | + Staining in some glandular trichomes | + Weak staining in pith and xylem | − | +++ | +++ |

Tissues in which GUS enzyme activity were detected in three different $T_0$ transgenic cotton plants transformed with the pFb8-like(150F2)-GUS construct. +, weak or localised expression, ++ medium expression, +++ very strong expression.

Intense staining was observed in both 10 and 20 dpa fibers. Another boll sample was taken at 30 dpa which showed even more intense staining. Staining in other parts of the plant was restricted to small glandular trichomes usually located above a small vein and occasionally hair trichomes distributed over the epidermal surfaces of the green parts of the plant. The hair trichomes were in general not stained but a small number could be occasionally stained along major veins or near cut edges. Staining was more intense on older parts of the plant, for example little or no staining was observed in the glandular trichomes of small young expanding leaves but the glandular trichomes of fully expanded leaves was strong. There were more glands stained on the abaxial surface than the adaxial surface of leaves. Staining in glands and sometimes trichomes was more intense near a cut edge. Cotyledon pieces stained strongly, especially around the vasculature although a few glandular trichomes were also intensely stained. No staining was observed in roots. Some weak staining was observed in the pith and parenchyma but mostly near cut edges.

The Fb8-like (150F2) promoter also appears to be wound inducible as indicated by GUS staining around cut edges of leaves and around areas of damage caused by insect feeding (thrips). A representative example is shown in FIG. 6.

The Fb8-like(150F2) promoter appears to be highly fiber preferential although there is some expression in small glandular trichomes on other parts of the plant possible during the later stages of development of those glands. The promoter is also wound inducible and this is consistent with the Fb8-like gene being involved in rapid cell wall growth and thickening involved in the various process of fiber expansion and maturation, secretary gland maturation and cell wall repair after wounding.

EXAMPLE 5

Expression of a Construct Comprising pFb8-Like Operably Linked to GUS in T1 Plants T1 seeds from four independent primary transformants with high expression in 10 or 20 dpa fiber were collected and planted in the glasshouse. These lines were T424-3, T424-42, T424-46 and T424-77. Sections of cotyledons were stained with X-Gluc as previously described. Gus activity was observed in just a few of the small glandular trichomes that are distributed across the cotyledon and from cut areas particularly along the vasculature typical of a wounding response.

Two T1 plants from each line were grown to maturity and flowers tagged to collect bolls of different ages (0, 10, 20 and 30 dpa) and various other tissues harvested including leaf, petiole, stem, root, bollcoat (at 10 and 20 dpa), small flower bud and various flower parts at 0 dpa (including flower bract, petal, stamens and stigma). These were stained for GUS activity. GUS staining was in X-Gluc solution overnight at 37° C. as described previously. Tissues were cleared in an ethanol series until no more chlorophyll was extracted and photographed. All lines had similar staining patterns, but that for line T424-3 summarized in Table 3.

| Tissue | Comment |
| --- | --- |
| 0 dpa ovule | Ovule surface only very weakly stained |
| 10 dpa fiber and ovule | Fibers moderately stained |
| 20 dpa fiber | Fibers moderately stained |
| 30 dpa fiber | Fibers intensely stained |
| Cotyledon | Some small glandular trichomes stained, stronger staining from cut edges mostly following the vasculature. No trichomes stained. |
| Leaf | Small glandular trichomes stained on young leaves, few on older leaves, stronger staining only at cut edges or around sites of damage to the leaves at all ages, no hair trichomes stained on any leaves. |
| Leaf Petiole | Staining throughout the petiole but only at the cut ends, hair trichomes not stained |
| Stem | Stronger staining throughout the stem but only from cut ends, no trichomes stained |
| Root | No staining |
| Boll Coat (0, 10 and 20 dpa) | Weak staining of the bollcoat septum separating locules and at some cut edges |
| Flower bud | Staining from the cut end of the pedicel and other wound sites |
| Flower Bract | Staining from the cut end, staining of a few glandular trichomes, but not hair trichomes. |
| Petal | Intense staining of small glandular trichomes at the base of the petal and only along one edge where the petals overlap. Petal trichomes not stained. No staining elsewhere on the petal. |

| Tissue | Comment |
|---|---|
| Stamen/Anther/Pollen | Very strong staining in pollen, weaker staining of anther wall, but not the filament |
| Stigma/Style | Very weak staining of stigma surface |

Overall, these data support that the Fb8-like promoter is fiber-preferential and expressed throughout fiber development, but is more active during the later stages of secondary cell wall deposition. It is expressed elsewhere in the plant, but usually in a relatively small number of specialized cells or tissues, including small glandular trichomes on young leaves, cotyledons and petals. The promoter appears to be wound responsive in a variety of tissues.

References

Al-Ghazi Y, Bourot S, Arioli T, Dennis E S, Llewellyn D J (2009) Transcript profiling during fiber development identifies pathways in secondary metabolism and cell wall structure that may contribute to cotton fiber quality. Plant and Cell Physiology 50: 1364-1381.

Carrington & Freed 1990. Cap-independent enhancement of translation by a plant potyvirus 5' nontranslated region. J. Virology 64, p. 1590-1597.

Chaubet et al. (1992). Genes encoding a histone H3.3-like variant in *Arabidopsis* contain intervening sequences. J Molecular Biology 225(2):569-74.

Cornelissen and Vandewiele (1989). Both RNA level and translation efficiency are reduced by anti-sense RNA in transgenic tobacco. Nucleic Acids Research 17(3):833-43.

Delaney et al. (2007). The fiber specificity of the cotton FSltp4 gene promoter is regulated by an AT-rich promoter region and the AT-hook transcription factor GhAT1. Plant and Cell Physiology 48, 1426-1437.

Eisner, T. et al. (1998). When defence backfires: detrimental effect of a plant's protective trichomes on an insect beneficial to the plant. Proceeding of the National Academy of Sciences, USA 95, p. 4410-4414.

Hsu et al. (1999). Analysis of promoter activity of cotton lipid transfer protein gene LTP6 in transgenic tobacco plants. Plant Science 143, p. 63-70.

Jefferson, R. A., Kavanagh, T. A. and Bevan, M. W. (1987) GUS fusions: β-glucuronidase as a sensitive and versatile gene fusion marker in higher plants. EMBO J. 6: 3901-3907.

John and Keller (1996). Metabolic pathway engineering in cotton: biosynthesis of polyhydroxybutyrate in fiber cell. Proceeding of the National Academy of Sciences, USA 93, 12678-12773.

Kim and Triplett, 82001). Cotton fiber growth in planta and in vitro. Models for plant cell elongation and cell wall biogenesis. Plant Physiology 127, p. 1361-1366.

Lazo, G. R., Stein, P. A., and Ludwig, R. A. (1991) A DNA transformation-competent *Arabidopsis* genomic library in *Agrobacterium*. Biotechnology 9: 963-967.

Li et al. (2005). The cotton ACTIN1 gene is functionally expressed in fibers and participates in fiber elongation. The Plant Cell 17, p. 859-875.

Lindbo, J. A. (2007). High-efficiency protein expression in plants from agroinfection-compatible Tobacco mosaic virus expression vectors. BMC Biotechnology 2007 Aug. 27; 7:52.

Liu et al. (2000). Cloning and promoter analysis of the cotton lipid transfer protein gene Ltp3. Biochimica et Biophysica Acta 1487, p. 106-111.

Liu, D., Zhang, X., Tu, L., Zhu, L., Guo X. (2006) Isolation by suppression-subtractive hybridization of genes preferentially expressed during early and late fiber development stages in cotton. Molecular Biology 40: 741-749.

Luo et al. (2007). GhDET2, a steroid 5a-reductase, plays an important role in cotton fiber cell initiation and elongation. The Plant Journal 51, p. 419-430.

Medeiros and Tingey, (2006). Glandular trichomes of *Solanum berthaultii* and its hybrids with *Solanum tuberosum* affect nymphal emergence, development, and survival of *Empoasca fabae* (Homoptera: Cicadellidae). Journal of Economic Entomology 99, p. 1483-1489.

Murray, F., Llewellyn, D., McFadden, H., Last, D., Dennis, E. S. and Peacock, W. J. (1999). Expression of the *Talaromyces flavus* glucose oxidase gene in cotton and tobacco reduces fungal infection, but is also phytotoxic. Molecular Breeding 5: 219-232.

Needleman and Wunsch (1970). A general method applicable to the search for similarities in the amino acid sequence of two proteins. J. Molecular Biology, 48, p. 443-453.

Pearson and Lipman (1988). Improved tools for biological sequence comparison. Proceeding of the National Academy of Sciences, USA 85, p. 2444-48.

Ranger and Hower, 2001. Role of the glandular trichomes in resistance of perennial alfalfa to the potato leafhopper (Homoptera: Cicadellidae). Journal of Economic Entomology 94, p. 950-957.

Ruan et al. (2003). Suppression of sucrose synthase gene expression represses cotton fiber cell initiation, elongation, and seed development. The Plant Cell 15, p. 952-964.

Sambrook, J. F., Russell, D. W. and Irwin, N. (2000). Molecular Cloning: A Laboratory Manual, $3^{rd}$ edition Volumes 1, 2, and 3. Cold Spring Harbor Laboratory Press.

Schünmann PHD, Llewellyn D, Surin B, Boevink P, Defeyter R C, Waterhouse P M (2003) A suite of novel promoters and terminators for plant biotechnology. Functional Plant Biology 30: 443-452.

Shangguan et al. (2008). Promoter of a cotton fiber MYB gene functional in trichomes of *Arabidopsis* and glandular trichomes of tobacco. Journal of Experimental Botany 59(13), p. 3533-3542.

Siomi, H. and Siomi, M. (2009). On the road to reading the RNA-interference code. Nature 457, 396-404.

Song et al. (2000). Expression of two tissue-specific promoters in transgenic cotton plants. Journal of Cotton Science 4, p. 217-223.

Szymanski et al. (2000). Progress in the molecular genetic analysis of trichome initiation and morphogenesis in *Arabidopsis*. Trends in Plant Science 5, p. 214-219.

Wagner et al. (2004). New approaches for studying and exploiting an old protuberance, the plant trichome. Annals of Botany 93, p. 3-11.

Wan C Y, Wilkins T A (1994) A modified hot borate method significantly enhances the yield of high-quality RNA from cotton (*Gossypium hirsutum* L.). Analytical Biochemistry 223: 7-12.

Wang, S. et al. (2004). Control of plant trichome development by a cotton fiber MYB gene. The Plant Cell 16, p. 2323-2334.

Waterman, M. S. (1995). Introduction to Computational Biology: Maps, sequences and genomes. Chapman & Hall. London.

Werker, E. (2000). Trichome diversity and development. Advances in Botanical Research 31, p. 1-35.

The invention claimed is:

1. A chimeric gene comprising
   (a) a promoter region consisting of the nucleotide sequence of SEQ ID NO: 1 from nucleotide 1 to nucleotide 1437, operably linked to
   (b) a nucleic acid sequence encoding a heterologous expression product of interest, and
   (c) a transcription termination and polyadenylation sequence.

2. The chimeric gene of claim 1, wherein said expression product of interest is a protein or said expression product of interest is an RNA molecule capable of modulating the expression of a gene endogenous to a plant.

3. The chimeric gene of claim 1, wherein said expression product is a reporter gene or a fiber-specific gene.

4. The chimeric gene of claim 2, wherein said RNA molecule comprises a nucleic acid sequence which yields a double-stranded RNA molecule that down-regulates expression of the endogenous gene.

5. A vector comprising the chimeric gene of claim 1.

6. A transgenic plant cell comprising the chimeric gene of claim 1.

7. The transgenic plant cell of claim 6, which is a cotton plant cell.

8. A transgenic plant comprising the chimeric gene of claim 1 stably integrated in its genome.

9. The transgenic plant of claim 8, which is a cotton plant.

10. The transgenic plant of claim 9, which is *G. hirsutum, G. barbadense, G. arboreum* or *G. herbaceum*.

11. A seed generated from the transgenic plant according to claim 8, wherein the seed comprises the chimeric gene.

12. A cotton fiber obtained from the transgenic plant of claim 9 comprising the chimeric gene.

13. A method of producing a transgenic plant comprising
    (a) providing the chimeric gene according to claim 1; and
    (b) introducing said chimeric gene in a plant.

14. A method of growing cotton comprising
    (a1) providing the transgenic plant of claim 8;
    (b) growing the plant of (a1); and
    (c) harvesting cotton produced by said plant.

15. A method of producing a seed comprising the chimeric gene of claim 1 comprising (a) growing a transgenic plant comprising the chimeric gene of claim 1, wherein said transgenic plant produces said seed and said chimeric gene is comprised in said seed, and (b) isolating said seed from said transgenic plant.

16. The method of claim 13, wherein said plant is a cotton plant.

17. A method of effecting fiber-preferential expression of a product in cotton comprising (a) introducing the chimeric gene of claim 1 into the genome of a cotton plant; or (b) providing the transgenic plant of claim 8.

18. A method of altering fiber properties in a cotton plant comprising (a) introducing the chimeric gene of claim 1 into the genome of a cotton plant; or (b) providing the transgenic plant of claim 8.

19. The method of claim 17, further comprising growing said plant until seeds are generated.

* * * * *

SEQUENCE LISTING

<160> NUMBER OF SEQ ID NOS: 15

<210> SEQ ID NO 1
<211> LENGTH: 1437
<212> TYPE: DNA
<213> ORGANISM: Gossypium hirsutum

<400> SEQUENCE: 1

```
catgattagt tagatcaagc ttttgagtct tcaaaaacat aaaaattaca aaaaaaaaac      60
aaacttaaaa tcatttatca atttgaacaa caaagcttgg ccgaatgcta agagcttaaa     120
aatggcttct tttgtttctt tttgttgcaa acggtggaga gaagagggaa atgaagattg     180
accatatttt tttattatgt tttaacatat aatattaata atttaatcat aattatactt     240
tggtgaatgt gacagtgggg agatacgtaa agtatataac attatacttt ttgcaagcag     300
ttggctggtc tacccaagag tgatcaaagt ttgagctgcc ttcaatgagc cattttttgc     360
ccataatgga taaaggcaat tgtttagtt caactgctca cagaataatg ttaaaatgaa      420
attaaaataa ggtggcctgg tcacacacac aaaaaaaaac taatgttggt tggttgaatt     480
ttatattacg gaatgtaata ttatatttta aaataaaatt atgttattta gattcttaat     540 atttgagca ttccatacta taatttcgta tacataatat taaaatatag taatataaag      600
tgtaattaac tttaaattac aagcataata ttaaattttg aatcaattaa tttttatttc     660
tattatttta attaatttag tctatttttt caaaataaaa tttaaatcta ataaaaata     720 attttccctt aatgttgaaa caactcatgt tatacttcaa aattataagt attatattta     780
ccttgatgat ttatttatta gtatattaat tctgattata attatggtgg gatacaatcg     840
ctttccacta aatattttaa ctatgattta taaatttatt tcaacatcgt atatttactt     900
attaatacat aatttatcat aattttatgg aaattgagac caagaaacat taagagaaca     960
aattctataa caaagacaat ttagaaaaaa atgtacttttt aggtaattttt aagtactctt    1020 aaccaaacac aaaaattcaa atcaaatgaa ctaaataaga taatataaca tacggaacat    1080
cttacttgta atcttacatt cccataattt tattatgaaa aataatctta tattactcga    1140
actaaatgtt gtcacaaatt attatctaaa taaagaaaaa cacttaattt ttataacatt    1200
ttttcatata tttgaaagat tatattttgt atatttacgt aaaaatattt gacatagatt    1260
gagcaccttc ttaacataat cccaccataa gtcaagtatg tagatgagaa attggtacaa    1320
acaacgtggg gccaaatccc accaaaccat ctctcattct ctcctataaa aggcttgcta    1380
cacatagaca acaatccaca cacaaataca cgttcttttc tttctatttg attaacc       1437
```

<210> SEQ ID NO 2
<211> LENGTH: 28
<212> TYPE: DNA
<213> ORGANISM: Artificial Sequence
<220> FEATURE:
<223> OTHER INFORMATION: primer Fb8-like_F

<400> SEQUENCE: 2

```
attcttttct ttctatttgg ttaaccat                                          28
```

<210> SEQ ID NO 3
<211> LENGTH: 20
<212> TYPE: DNA
<213> ORGANISM: Artificial Sequence
<220> FEATURE:
<223> OTHER INFORMATION: primer Fb8-like_R

<400> SEQUENCE: 3
tagtgctcga gccagactga                                                  20

<210> SEQ ID NO 4
<211> LENGTH: 20
<212> TYPE: DNA
<213> ORGANISM: Artificial Sequence
<220> FEATURE:
<223> OTHER INFORMATION: primer QFb8like_F

<400> SEQUENCE: 4
gagtgccaag agtcacacga                                                  20

<210> SEQ ID NO 5
<211> LENGTH: 20
<212> TYPE: DNA
<213> ORGANISM: Artificial Sequence
<220> FEATURE:
<223> OTHER INFORMATION: primer QFb8like_R

<400> SEQUENCE: 5
ttggatccca cccttaaaca                                                  20

<210> SEQ ID NO 6
<211> LENGTH: 20
<212> TYPE: DNA
<213> ORGANISM: Artificial Sequence
<220> FEATURE:
<223> OTHER INFORMATION: primer UbiQ_F

<400> SEQUENCE: 6
aatccacttt gcacctggtc                                                  20

<210> SEQ ID NO 7
<211> LENGTH: 20
<212> TYPE: DNA
<213> ORGANISM: Artificial Sequence
<220> FEATURE:
<223> OTHER INFORMATION: primer UbiQ_R

<400> SEQUENCE: 7
ctagtggcca gctcacatca                                                  20

<210> SEQ ID NO 8
<211> LENGTH: 20
<212> TYPE: DNA
<213> ORGANISM: Artificial Sequence
<220> FEATURE:
<223> OTHER INFORMATION: primer 150F2_F

<400> SEQUENCE: 8
tggctcatag cattcgtcac                                                  20

<210> SEQ ID NO 9
<211> LENGTH: 20
<212> TYPE: DNA
<213> ORGANISM: Artificial Sequence
<220> FEATURE:
<223> OTHER INFORMATION: primer 150F2_R

<400> SEQUENCE: 9
ccaattgtgg gagctctgat                                                  20

<210> SEQ ID NO 10
<211> LENGTH: 2739
<212> TYPE: DNA

<213> ORGANISM: Artificial Sequence
<220> FEATURE:
<223> OTHER INFORMATION: promoter and gene for BAC150F2

<400> SEQUENCE: 10

```
agtccctaag ttcaaaacta taaattttca ctttagaaat taatcatttt tcacatctaa      60
gcatcaaatt taaccaaatg acacaaattt catgattagt tagatcaagc ttttgagtct     120
tcaaaaacat aaaaattaca aaaaaaaaac aaacttaaaa tcatttatca atttgaacaa     180
caaagcttgg ccgaatgcta agagcttaaa aatggcttct tttgtttctt tttgttgcaa     240
acggtggaga gaagagggaa atgaagattg accatatttt tttattatgt tttaacatat     300
aatattaata atttaatcat aattatactt tggtgaatgt gacagtgggg agatacgtaa     360
agtatataac attatacttt ttgcaagcag ttggctggtc tacccaagag tgatcaaagt     420
ttgagctgcc ttcaatgagc caattttttgc ccataatgga taaaggcaat ttgtttagtt     480
caactgctca cagaataatg ttaaaatgaa attaaaataa ggtggcctgg tcacacacac     540
aaaaaaaaac taatgttggt tggttgaatt ttatattacg gaatgtaata ttatatttta     600
aaataaaatt atgttatttta gattcttaat attttgagca ttccatacta taatttcgta     660
tacataatat taaaatatag taatataaag tgtaattaac tttaaattac aagcataata     720
ttaaattttg aatcaattaa tttttatttc tattattttta attaatttag tctattttt     780
caaaataaaa tttaaatcta aataaaaata attttttcctt aatgttgaaa caactcatgt     840
tatacttcaa aattataagt attatattta ccttgatgat ttatttatta gtatattaat     900
tctgattata attatggtgg gatacaatcg ctttccacta aatattttaa ctatgattta     960
taaatttatt tcaacatcgt atatttactt attaatacat aatttatcat aattttatgg    1020
aaattgagac caagaaacat taagagaaca aattctataa caaagacaat ttagaaaaaa    1080
atgtactttt aggtaatttt aagtactctt aaccaaacac aaaaattcaa atcaaatgaa    1140
ctaaataaga taatataaca tacggaacat cttacttgta atcttacatt cccataattt    1200
tattatgaaa aataatctta tattactcga actaaatgtt gtcacaaatt attatctaaa    1260
taaagaaaaa cacttaattt ttataacatt ttttcatata tttgaaagat tatattttgt    1320
atatttacgt aaaaatattt gacatagatt gagcaccttc ttaacataat cccaccataa    1380
gtcaagtatg tagatgagaa attggtacaa acaacgtggg gccaaatccc accaaaccat    1440
ctctcattct ctcctataaa aggcttgcta cacatagaca acaatccaca cacaaataca    1500
cgttcttttc tttctatttg attaaccatg gctcatagca ttcgtcaccc tttcttcctt    1560
ttccaacttt tactcataag tgtctcacta gtgaccggta gccacactgt ttcggcagcg    1620
gctcgacgtt tattcgagac acaagcaacc tcatcgagagc tcccacaatt ggcttcaaaa    1680
tacgaaaagc acgaagagtc tgaatacgaa aagccagaat acaaacagcc aaagtatcac    1740
gaagagtact caaaacttga gaagcctgaa atgcaaaagg aggaaaaaca aaaaccctgc    1800
aaacagcatg aagagtacca cgagtcacac gaatcaaagg agcaaaaaga gtacgagaaa    1860
gaaaatctcg agttccccaa atgggaaaag cctaaagagc acgagaaaca cgaagtcgaa    1920
tatccgaaaa tacccgagta caaggtaaaa caagatgagg gcaaggaaca taaacatgaa    1980
gagtaccacg aatcacgcga atcgaaagag cacgaagagt acgagaaaga aaacccgag    2040
ttccctaaat tggaaaagcc taaagagcac gagaaacacg aagtcgaata tccggaaata    2100
cccgaataca agaaaaagca agatgagggt aacgaacata acatgagtt cccaaagcat    2160
gaaaagaag aggagaagaa acctgagaaa aaggcagagt accttgagtg ggctaaaatg    2220
```

```
cctgaatggt cgaagtccat gtttactcag cctggctcgg ccactaagcc ttgaatcata    2280
tgacactggt gcatgtgcca tcatcatgca gtaatttcat ggtatatcgt aatatatagt    2340
taataaaaaa gatggtgatt gggaaatgtg tgtgtgcatt cctccatgca ctaatggtga    2400
atctctttgc atacatagaa attctaaatg gttatagttt atgttatagt gtatgttgta    2460
gtgaaattaa ttttaaatgt tgtatctaat gttaacatca cttggcttga tttatgttat    2520
gttatgtatt ttactttaat gatattgcat gtattgttaa tttaacattg cttgatcatt    2580
atactcttct actattaatt ataaatggca ctgttttgtt taaacttttt acaagttaag    2640
acatgtataa atatatgaca atataattac aagttttagt tcaatgttag ctatcttagt    2700
atgttattga tgatcttaat tacatttaaa caaattcca                           2739
```

<210> SEQ ID NO 11
<211> LENGTH: 57
<212> TYPE: DNA
<213> ORGANISM: Artificial Sequence
<220> FEATURE:
<223> OTHER INFORMATION: primer gwFb8-likePro(150F2)_F

<400> SEQUENCE: 11

```
ggggacaagt ttgtacaaaa aagcaggctc atgattagtt agatcaagct tttgagt        57
```

<210> SEQ ID NO 12
<211> LENGTH: 57
<212> TYPE: DNA
<213> ORGANISM: Artificial Sequence
<220> FEATURE:
<223> OTHER INFORMATION: primer gwFb8-likePro(150F2)_R

<400> SEQUENCE: 12

```
ggggaccact ttgtacaaga aagctgggtg gttaatcaaa tagaaagaaa agaacgt        57
```

<210> SEQ ID NO 13
<211> LENGTH: 248
<212> TYPE: PRT
<213> ORGANISM: Gossypium hirsutum

<400> SEQUENCE: 13

```
Met Ala His Ser Ile Arg His Pro Phe Phe Leu Phe Gln Leu Leu Leu
1               5                   10                  15

Ile Ser Val Ser Leu Val Thr Gly Ser His Thr Val Ser Ala Ala Ala
            20                  25                  30

Arg Arg Leu Phe Glu Thr Gln Ala Thr Ser Ser Glu Leu Pro Gln Leu
        35                  40                  45

Ala Ser Lys Tyr Glu Lys His Glu Glu Ser Glu Tyr Glu Lys Pro Glu
    50                  55                  60

Tyr Lys Gln Pro Lys Tyr His Glu Glu Tyr Ser Lys Leu Glu Lys Pro
65                  70                  75                  80

Glu Met Gln Lys Glu Glu Lys Gln Lys Pro Cys Lys Gln His Glu Glu
                85                  90                  95

Tyr His Glu Ser His Glu Ser Lys Glu Gln Lys Glu Tyr Glu Lys Glu
            100                 105                 110

Asn Leu Glu Phe Pro Lys Trp Glu Lys Pro Lys Glu His Glu Lys His
        115                 120                 125

Glu Val Glu Tyr Pro Lys Ile Pro Glu Tyr Lys Val Lys Gln Asp Glu
    130                 135                 140

Gly Lys Glu His Lys His Glu Glu Tyr His Glu Ser Arg Glu Ser Lys
```

```
        145                 150                 155                 160
    Glu His Glu Glu Tyr Glu Lys Glu Lys Pro Glu Phe Pro Lys Leu Glu
                    165                 170                 175
    Lys Pro Lys Glu His Glu Lys His Glu Val Glu Tyr Pro Glu Ile Pro
                    180                 185                 190
    Glu Tyr Lys Lys Lys Gln Asp Glu Gly Asn Glu His Lys His Glu Phe
                    195                 200                 205
    Pro Lys His Glu Lys Glu Glu Lys Lys Pro Glu Lys Lys Ala Glu
                210                 215                 220
    Tyr Leu Glu Trp Ala Lys Met Pro Glu Trp Ser Lys Ser Met Phe Thr
    225                 230                 235                 240
    Gln Pro Gly Ser Ala Thr Lys Pro
                    245

<210> SEQ ID NO 14
<211> LENGTH: 276
<212> TYPE: PRT
<213> ORGANISM: Gossypium hirsutum

<400> SEQUENCE: 14

Met Ala His Asn Phe Arg His Pro Phe Phe Leu Phe Gln Leu Leu Leu
    1               5                  10                  15
    Ile Thr Val Ser Leu Met Ile Gly Ser His Thr Val Ser Ser Ala Ala
                    20                  25                  30
    Arg His Leu Phe His Thr Gln Thr Thr Ser Ser Glu Leu Pro Gln Leu
                    35                  40                  45
    Ala Ser Lys Tyr Glu Lys His Glu Glu Ser Glu Tyr Lys Gln Pro Lys
    50                  55                  60
    Tyr His Glu Glu Tyr Pro Lys His Glu Lys Pro Glu Met Tyr Lys Glu
    65                  70                  75                  80
    Glu Lys Gln Lys Pro Cys Lys His His Glu Glu Tyr His Glu Ser Arg
                    85                  90                  95
    Glu Ser Lys Glu His Glu Glu Tyr Asp Lys Glu Lys Pro Asp Phe Pro
                    100                 105                 110
    Lys Trp Glu Lys Pro Lys Glu His Glu Lys His Glu Val Glu Tyr Pro
                    115                 120                 125
    Lys Ile Pro Glu Tyr Lys Asp Lys Gln Asp Glu Asp Lys Glu His Lys
                130                 135                 140
    Asn Glu Glu Tyr His Glu Ser Arg Glu Ser Lys Glu His Glu Glu Tyr
    145                 150                 155                 160
    Glu Lys Glu Lys Pro Glu Phe Pro Lys Arg Glu Lys Pro Lys Glu His
                    165                 170                 175
    Glu Lys His Glu Val Glu Tyr Ser Glu Ile Pro Glu Tyr Lys Glu Arg
                    180                 185                 190
    Glu Asp Lys Ser Lys Lys His Lys Asp Glu Glu Cys Gln Glu Ser His
                    195                 200                 205
    Glu Ser Lys Glu His Glu Glu Tyr Glu Lys Glu Lys Pro Asp Phe Pro
                    210                 215                 220
    Lys Trp Glu Lys Pro Lys Gly His Glu Lys His Lys Ala Glu Tyr Pro
    225                 230                 235                 240
    Lys Ile Pro Glu Cys Lys Glu Lys Leu Asp Glu Asp Lys Glu His Lys
                    245                 250                 255
    His Glu Phe Pro Lys His Glu Lys Glu Glu Lys Lys Pro Glu Lys
                    260                 265                 270
```

Gly Ile Val Pro
     275

<210> SEQ ID NO 15
<211> LENGTH: 15390
<212> TYPE: DNA
<213> ORGANISM: Artificial Sequence
<220> FEATURE:
<223> OTHER INFORMATION: vector

<400> SEQUENCE: 15

| | | | | | |
|---|---|---|---|---|---|
| ttgtacaaag | tggtctcgat | cgaggaattc | gattcgacca | tggtccgtcc | tgtagaaacc | 60 |
| ccaacccgtg | aaatcaaaaa | actcgacggc | ctgtgggcat | tcagtctgga | tcgcgaaaac | 120 |
| tgtggaattg | atcagcgttg | gtgggaaagc | gcgttacaag | aaagccgggc | aattgctgtg | 180 |
| ccaggcagtt | ttaacgatca | gttcgccgat | gcagatattc | gtaattatgc | gggcaacgtc | 240 |
| tggtatcagc | gcgaagtctt | tataccgaaa | ggttgggcag | gccagcgtat | cgtgctgcgt | 300 |
| ttcgatgcgg | tcactcatta | cggcaaagtg | tgggtcaata | atcaggaagt | gatggagcat | 360 |
| cagggcggct | atacgccatt | tgaagccgat | gtcacgccgt | atgttattgc | cgggaaaagt | 420 |
| gtacgtatca | ccgtttgtgt | gaacaacgaa | ctgaactggc | agactatccc | gccgggaatg | 480 |
| gtgattaccg | acgaaaacgg | caagaaaaag | cagtcttact | tccatgattt | ctttaactat | 540 |
| gccggaatcc | atcgcagcgt | aatgctctac | accacgccga | acacctgggt | ggacgatatc | 600 |
| accgtggtga | cgcatgtcgc | gcaagactgt | aaccacgcgt | ctgttgactg | gcaggtggtg | 660 |
| gccaatggtg | atgtcagcgt | tgaactgcgt | gatgcggatc | aacaggtggt | tgcaactgga | 720 |
| caaggcacta | gcgggacttt | gcaagtggtg | aatccgcacc | tctggcaacc | gggtgaaggt | 780 |
| tatctctatg | aactgtgcgt | cacagccaaa | agccagacag | agtgtgatat | ctacccgctt | 840 |
| cgcgtcggca | tccggtcagt | ggcagtgaag | gcgaacagt | tcctgattaa | ccacaaaccg | 900 |
| ttctacttta | ctggctttgg | tcgtcatgaa | gatgcggact | acgtggcaa | aggattcgat | 960 |
| aacgtgctga | tggtgcacga | ccacgcatta | atggactgga | ttggggccaa | ctcctaccgt | 1020 |
| acctcgcatt | acccttacgc | tgaagagatg | ctcgactggg | cagatgaaca | tggcatcgtg | 1080 |
| gtgattgatg | aaactgctgc | tgtcggcttt | aacctctctt | taggcattgg | tttcgaagcg | 1140 |
| ggcaacaagc | cgaaagaact | gtacagcgaa | gaggcagtca | acggggaaac | tcagcaagcg | 1200 |
| cacttacagg | cgattaaaga | gctgatagcg | cgtgacaaaa | accacccaag | cgtggtgatg | 1260 |
| tggagtattg | ccaacgaacc | ggatacccgt | ccgcaagtgc | acgggaatat | ttcgccactg | 1320 |
| gcggaagcaa | cgcgtaaact | cgacccgacg | cgtccgatca | cctgcgtcaa | tgtaatgttc | 1380 |
| tgcgacgctc | acaccgatac | catcagcgat | ctctttgatg | tgctgtgcct | gaaccgttat | 1440 |
| tacggatggt | atgtccaaag | cggcgatttg | gaaacggcag | agaaggtact | ggaaaaagaa | 1500 |
| cttctggcct | ggcaggagaa | actgcatcag | ccgattatca | tcaccgaata | cggcgtggat | 1560 |
| acgttagccg | ggctgcactc | aatgtacacc | gacatgtgga | gtgaagagta | tcagtgtgca | 1620 |
| tggctggata | tgtatcaccg | cgtctttgat | cgcgtcagcg | ccgtcgtcgg | tgaacaggta | 1680 |
| tggaatttcg | ccgattttgc | gacctcgcaa | ggcatattgc | gcgttggcgg | taacaagaaa | 1740 |
| gggatcttca | ctcgcgaccg | caaaccgaag | tcggcggctt | ttctgctgca | aaaacgctgg | 1800 |
| actggcatga | acttcggtga | aaaccgcag | cagggaggca | aacaatgaat | caacaactct | 1860 |
| cctggcgcac | catcgtcggc | tacagcctcg | ggaattcctg | cagcccgggg | gatccgctag | 1920 |
| cgtttagcgg | gggaaaaagg | acagttgatc | tgttgctgtt | tgcaatttttt | taagggtat | 1980 |

-continued

```
gttgtcagat gcatgttgta atgcttgttc atcaacacat tatatgactt gcagttgctg    2040
atgatggaaa cttaaagctt aatactactt tgtttattc acttacaaat accggttggg     2100
ttctttgttt atcaggaatg ctcattgtat gtagctaaaa gctggccgtt tatagtttta    2160
ttgccctaaa tctggtactt tatccaaaaa ctaaatttgg aaacatcaaa tactttttc     2220 aagaatgata aactcgtaca ctctctaggg tactcctgaa atttaaatca aaatccaaaa    2280
ccgcttagga aggaacatat gtgataagaa ctgaaatttc gattaactat tacaagatag    2340
tcggcccaat tcgagaggac tagtctccga ttacaaggag taaatatctt aatcttgata    2400
aacaaaacac atataaaaaa cctaaaaata taggaacata atacataaac taaaagttgt    2460
gggaacagtt acaaatctgc agtctcactc cctaaatttg tgagtcacct ttcacctcca    2520
agttttcgaa tgttctccca ccattccactt tccctccacc cggattccct ccaattaata   2580
gctgacacaa cccgttttga cccaacattg ggttcgtatc aatacatccg gcccggaaaa    2640
tcgacttgtc ctcaagtcga aaggagggga attattgtgc caagcaaaaa gccattcgat    2700
tggaggttga tggatgattt ccttgtgttt gaaagcttca aaagatccgg ccaaatcagc    2760
ttttaatgcc tcttgaactg tagccacaac accactttga aacctcaaat ctgttttcaa    2820
ttgggatcca ctagttctag agcggccgct ctagtcgagt ctagaaagct tccaacaaaa    2880
acataacaca ccgcttcgcg gagtaattca aagaataata acaactcttt attcattaat    2940
cacaattaca tctcataatt ctatcttaat agaacctcta tcaattacaa tagacataaa    3000
ctcaataccg tcgacccggg gtgggcgaag aactccagca tgagatcccc gcgctggagg    3060
atcatccagc cggcgtcccg gaaaacgatt ccgaagccca acctttcata gaaggcggcg    3120
gtggaatcga aatctcgtga tggcaggttg ggcgtcgctt ggtcggtcat ttcgaacccc    3180
agagtcccgc tcagaagaac tcgtcaagaa ggcgatagaa ggcgatgcgc tgcgaatcgg    3240
gagcggcgat accgtaaagc acgaggaagc ggtcagccca ttcgccgcca agctcttcag    3300
caatatcacg ggtagccaac gctatgtcct gatagcggtc cgccacaccc agccggccac    3360
agtcgatgaa tccagaaaag cggccatttt ccaccatgat attcggcaag caggcatcgc    3420
catgggtcac gacgagatcc tcgccgtcgg gcatgcgcgc cttgagcctg gcgaacagtt    3480
cggctggcgc gagcccctga tgctcttcgt ccagatcatc ctgatcgaca agaccggctt    3540
ccatccgagt acgtgctcgc tcgatgcgat gtttcgcttg gtggtcgaat gggcaggtag    3600
ccggatcaag cgtatgcagc cgccgcattg catcagccat gatggatact ttctcggcag    3660
gagcaaggtg agatgacagg agatcctgcc ccggcacttc gcccaatagc agccagtccc    3720
ttcccgcttc agtgacaacg tcgagcacag ctgcgcaagg aacgcccgtc gtggccagcc    3780
acgatagccg cgctgcctcg tcctgcagtt atcatcatca tcatagacac acgaaataaa    3840
gtaatcagat tatcagttaa agctatgtaa tatttacacc ataaccaatc aattaaaaaa    3900
tagatcagtt taaagaaaga tcaaagctca aaaaaataaa aagagaaaag ggtcctaacc    3960
aagaaaatga aggagaaaaa ctagaaattt acctgcagtt cattcagggc accggacagg    4020
tcggtcttga caaaaagaac cgggcgcccc tgcgctgaca gccggaacac ggcggcatca    4080
gagcagccga ttgtctgttg tgcccagtca tagccgaata gcctctccac ccaagcggcc    4140
ggagaacctg cgtgcaatcc atcttgttca atcattgtta tcggcgctat gaaattctga    4200
acaatctgtt cagaagcact ctatttatag acccaagaca acgcgtacta agtacgctaa    4260
ctagatctaa gtgtgaacgc tcttccgtca gattcgttca gcttaagcgc ttcactagca    4320
tcacagatcc tgagcgtcca cgtgtcattt aatccaaggg ctattatact agtcaactat    4380
```

```
tggtcaaatg tctctgatcc cggcacgggg gtaatactaa gccccgtgct gacgtaggca   4440
cggagacata tgacgtcatc aaaacgcttc gtttcattta tcacttaaca tatcgcttcg   4500
cggaattaaa ttaaaacaat aataatatat ctattatctt atttcagcca ctcacaactt   4560
gacacgttta cagccgcaat ttcactaacg cgccaaaacc aaattcaaat taagttata    4620
cgctgcttcg aggaagctag cttaaaaaac acagacgaag aacagaataa taataattct   4680
cattaatcca tataaaatta caacatagga tcctctagag cggccctaga attaattcag   4740
tacattaaaa acgtccgcaa tgtgttatta agttgtctaa gcgtcaattt gtttacacca   4800
caatatatcc tgccaccagc cagccaacag ctccccgacc ggcagctcgg cacaaaatca   4860
ccactcgata caggcagccc atcagtccgg gacggcgtca gcgggagagc cgttgtaagg   4920
cggcagactt tgctcatgtt accgatgcta ttcggaagaa cggcaactaa gctgccgggt   4980
ttgaaacacg gatgatctcg cggagggtag catgttgatt gtaacgatga cagagcgttg   5040
ctgcctgtga tcaaatatca tctccctcgc agagatccga attatcagcc ttcttattca   5100
tttctcgctt aaccgtgaca ggctgtcgat cttgagaact atgccgacat aataggaaat   5160
cgctggataa agccgctgag gaagctgagt ggcgctattt ctttagaagt gaacgttgac   5220
gatcgtcgac ggatcttttc cgctgcataa ccctgcttcg gggtcattat agcgattttt   5280
tcggtatatc catccttttt cgcacgatat acaggatttt gccaaagggt tcgtgtagac   5340
tttccttggt gtatccaacg gcgtcagccg ggcaggatag gtgaagtagg cccacccgcg   5400
agcgggtgtt ccttcttcac tgtccctttat tcgcacctgg cggtgctcaa cgggaatcct   5460
gctctgcgag gctggccggc taccgccggc gtaacagatg agggcaagcg gatggctgat   5520
gaaaccaagc caaccagggg tgatgctgcc aacttactga tttagtgtat gatggtgttt   5580
ttgaggtgct ccagtggctt ctgtttctat cagctgtccc tcctgttcag ctactgacgg   5640
ggtggtgcgt aacggcaaaa gcaccgccgg acatcagcgc tatctctgct ctcactgccg   5700
taaaacatgg caactgcagt tcacttacac cgcttctcaa cccggtacgc accagaaaat   5760
cattgatatg gccatgaatg gcgttggatg ccgggcaaca gcccgcatta tgggcgttgg   5820
cctcaacacg attttacgtc acttaaaaaa ctcaggccgc agtcggtaac ctcgcgcata   5880
cagccgggca gtgacgtcat cgtctgcgcg gaaatggacg aacagtgggg ctatgtcggg   5940
gctaaatcgc gccagcgctg gctgttttac gcgtatgaca gtctccggaa gacggttgtt   6000
gcgcacgtat tcggtgaacg cactatggcg acgctggggc gtcttatgag cctgctgtca   6060
cccctttgacg tggtgatatg gatgacggat ggctggccgc tgtatgaatc ccgcctgaag   6120
ggaaagctgc acgtaatcag caagcgatat acgcagcgaa ttgagcggca taacctgaat   6180
ctgaggcagc acctggcacg gctgggacgg aagtcgctgt cgttctcaaa atcggtggag   6240
ctgcatgaca aagtcatcgg gcattatctg aacataaaac actatcaata agttggagtc   6300
attacccaac caggaagggc agcccaccta tcaaggtgta ctgccttcca gacgaacgaa   6360
gagcgattga ggaaaaggcg gcggcggccg gcatgagcct gtcggcctac ctgctggccg   6420
tcggccaggg ctacaaaatc acgggcgtcg tggactatga gcacgtccgc gagctggccc   6480
gcatcaatgc cgacctgggc cgcctggcg gcctgctgaa actctggctc accgacgacc   6540
cgcgcacggc gcggttcggt gatgccacga tcctcgccct gctggcgaag atcgaagaga   6600
agcaggacga gcttggcaag gtcatgatgg gcgtggtccg cccgagggca gagccatgac   6660
tttttttagcc gctaaaacgg ccgggggggtg cgcgtgattg ccaagcacgt ccccatgcgc   6720
```

```
tccatcaaga agagcgactt cgcggagctg gtattcgtgc agggcaagat tcggaatacc   6780
aagtacgaga aggacggcca gacggtctac gggaccgact tcattgccga taaggtggat   6840
tatctggaca ccaaggcacc aggcgggtca aatcaggaat aagggcacat tgccccggcg   6900
tgagtcgggg caatcccgca aggagggtga atgaatcgga cgtttgaccg gaaggcatac   6960
aggcaagaac tgatcgacgc ggggttttcc gccgaggatg ccgaaaccat cgcaagccgc   7020
accgtcatgc gtgcgccccg cgaaaccttc cagtccgtcg gctcgatggt ccagcaagct   7080
acggccaaga tcgagcgcga cagcgtgcaa ctggctcccc ctgccctgcc cgcgccatcg   7140
gccgccgtgg agcgttcgcg tcgtctcgaa caggaggcgg caggtttggc gaagtcgatg   7200
accatcgaca cgcgaggaac tatgacgacc aagaagcgaa aaaccgccgg cgaggacctg   7260
gcaaaacagg tcagcgaggc caagcaggcc gcgttgctga acacacgaa gcagcagatc    7320
aaggaaatgc agctttcctt gttcgatatt gcgccgtggc cggacacgat gcgagcgatg   7380
ccaaacgaca cggcccgctc tgccctgttc accacgcgca acaagaaaat cccgcgcgag   7440
gcgctgcaaa acaaggtcat tttccacgtc aacaaggacg tgaagatcac ctacaccggc   7500
gtcgagctgc gggccgacga tgacgaactg gtgtggcagc aggtgttgga gtacgcgaag   7560
cgcacccta tcggcgagcc gatcaccttc acgttctacg agctttgcca ggacctgggc    7620
tggtcgatca atggccggta ttacacgaag gccgaggaat gcctgtcgcg cctacaggcg   7680
acggcgatgg gcttcacgtc cgaccgcgtt gggcacctgg aatcggtgtc gctgctgcac   7740
cgcttccgcg tcctggaccg tggcaagaaa acgtcccgtt gccaggtcct gatcgacgag   7800
gaaatcgtcg tgctgtttgc tggcgaccac tacacgaaat tcatatggga gaagtaccgc   7860
aagctgtcgc cgacggcccg acggatgttc gactatttca gctcgcaccg ggagccgtac   7920
ccgctcaagc tggaaaacctt ccgcctcatg tgcggatcgg attccacccg cgtgaagaag  7980
tggcgcgagc aggtcggcga agcctgcgaa gagttgcgag cagcggcct ggtggaacac    8040
gcctgggtca atgatgacct ggtgcattgc aaacgctagg gccttgtggg gtcagttccg   8100
gctgggggtt cagcagccag cgctttactg gcatttcagg aacaagcggg cactgctcga   8160
cgcacttgct tcgctcagta tcgctcggga cgcacgcgc gctctacgaa ctgccgataa    8220
acagaggatt aaaattgaca attgtgatta aggctcagat tcgacggctt ggagcggccg   8280
acgtgcagga tttccgcgag atccgattgt cggccctgaa gaaagctcca gagatgttcg   8340
ggtccgtta cgagcacgag gagaaaaagc ccatggaggc gttcgctgaa cggttgcgag    8400
atgccgtggc attcggcgcc tacatcgacg gcgagatcat tgggctgtcg gtcttcaaac   8460
aggaggacgg ccccaaggac gctcacaagg cgcatctgtc cggcgttttc gtggagcccg   8520
aacagcgagg ccgaggggtc gccggtatgc tgctgcgggc gttgccggcg gtttattgc    8580
tcgtgatgat cgtccgacag attccaacgg gaatctggtg gatgcgcatc ttcatcctcg   8640
gcgcacttaa tatttcgcta ttctggagct tgttgtttat ttcggtctac cgcctgccgg   8700
gcggggtcgc ggcgacggta ggcgctgtgc agccgctgat ggtcgtgttc atctctgccg   8760
ctctgctagg tagcccgata cgattgatgg cggtcctggg ggctatttgc ggaactgcgg   8820
gcgtggcgct gttggtgttg acaccaaacg cagcgctaga tcctgtcggc gtcgcagcgg   8880
gcctggcggg ggcggtttcc atggcgttcg gaaccgtgct gacccgcaag tggcaacctc   8940
ccgtgcctct gctcaccttt accgcctggc aactggcggc cggaggactt ctgctcgttc   9000
cagtagcttt agtgtttgat ccgccaatcc cgatgcctac aggaaccaat gttctcggcc   9060
tggcgtggct cggcctgatc ggagcgggtt taacctactt cctttggttc cgggggatct   9120
```

```
cgcgactcga acctacagtt gtttccttac tgggctttct cagccgggat ggcgctaaga   9180
agctattgcc gccgatcttc atatgcggtg tgaaataccg cacagatgcg taaggagaaa   9240
ataccgcatc aggcgctctt ccgcttcctc gctcactgac tcgctgcgct cggtcgttcg   9300
gctgcggcga gcggtatcag ctcactcaaa ggcggtaata cggttatcca cagaatcagg   9360
ggataacgca ggaaagaaca tgtgagcaaa aggccagcaa aaggccagga accgtaaaaa   9420
ggccgcgttg ctggcgtttt tccataggct ccgcccccct gacgagcatc acaaaaatcg   9480
acgctcaagt cagaggtggc gaaacccgac aggactataa agataccagg cgtttccccc   9540
tggaagctcc ctcgtgcgct ctcctgttcc gaccctgccg cttaccggat acctgtccgc   9600
ctttctccct tcgggaagcg tggcgctttc tcatagctca cgctgtaggt atctcagttc   9660
ggtgtaggtc gttcgctcca agctgggctg tgtgcacgaa ccccccgttc agcccgaccg   9720
ctgcgcctta tccggtaact atcgtcttga gtccaacccg gtaagacacg acttatcgcc   9780
actggcagca gccactggta acaggattag cagagcgagg tatgtaggcg gtgctacaga   9840
gttcttgaag tggtggccta actacggcta cactagaagg acagtatttg gtatctgcgc   9900
tctgctgaag ccagttacct tcggaaaaag agttggtagc tcttgatccg gcaaacaaac   9960
caccgctggt agcggtggtt tttttgtttg caagcagcag attacgcgca gaaaaaaagg  10020
atatcaagaa gatcctttga tcttttctac ggggtctgac gctcagtgga acgaaaactc  10080
acgttaaggg attttggtca tgagattatc aaaaaggatc ttcacctaga tccttttaaa  10140
ttaaaaatga agttttaaat caatctaaag tatatatgag taaacttggt ctgacagtta  10200
ccaatgctta atcagtgagg cacctatctc agcgatctgt ctatttcgtt catccatagt  10260
tgcctgactc cccgtcgtgt agataactac gatacgggag ggcttaccat ctggccccag  10320
tgctgcaatg ataccgcgag acccacgctc accggctcca gatttatcag caataaacca  10380
gccagccgga agggccgagc gcagaagtgg tcctgcaact ttatccgcct ccatccagtc  10440
tattaaacaa gtggcagcaa cggattcgca aacctgtcac gccttttgtg ccaaaagccg  10500
cgccaggttt gcgatccgct gtgccaggcg ttaggcgtca tatgaagatt tcggtgatcc  10560
ctgagcaggt ggcggaaaca ttggatgctg agaaccattt cattgttcgt gaagtgttcg  10620
atgtgcacct atccgaccaa ggctttgaac tatctaccag aagtgtgagc ccctaccgga  10680
aggattacat ctcggatgat gactctgatg aagactctgc ttgctatggc gcattcatcg  10740
accaagagct tgtcgggaag attgaactca actcaacatg gaacgatcta gcctctatcg  10800
aacacattgt tgtgtcgcac acgcaccgag gcaaggagt cgcgcacagt ctcatcgaat  10860
ttgcgaaaaa gtgggcacta agcagacagc tccttggcat acgattagag acacaaacga  10920
acaatgtacc tgcctgcaat ttgtacgcaa aatgtggctt tactctcggc ggcattgacc  10980
tgttcacgta taaaactaga cctcaagtct cgaacgaaac agcgatgtac tggtactggt  11040
tctcgggagc acaggatgac gcctaacaat tcattcaagc cgacaccgct tcgcggcgcg  11100
gcttaattca ggagttaaac atcatgaggg aagcggtgat cgccgaagta tcgactcaac  11160
tatcagaggt agttggcgtc atcgagcgcc atctcgaacc gacgttgctg ccgtacatt  11220 tgtacggctc cgcagtggat ggcggcctga agccacacag tgatattgat ttgctggtta  11280
cggtgaccgt aaggcttgat gaaacaacgc ggcgagcttt gatcaacgac cttttggaaa  11340
cttcggcttc ccctggagag agcgagattc tccgcgctgt agaagtcacc attgttgtgc  11400
acgacgacat cattccgtgg cgttatccag ctaagcgcga actgcaattt ggagaatggc  11460
```

```
agcgcaatga cattcttgca ggtatcttcg agccagccac gatcgacatt gatctggcta    11520
tcttgctgac aaaagcaaga gaacatagcg ttgccttggt aggtccagcg gcggaggaac    11580
tctttgatcc ggttcctgaa caggatctat ttgaggcgct aaatgaaacc ttaacgctat    11640
ggaactcgcc gcccgactgg gctggcgatg agcgaaatgt agtgcttacg ttgtcccgca    11700
tttggtacag cgcagtaacc ggcaaaatcg cgccgaagga tgtcgctgcc gactgggcaa    11760
tggagcgcct gccggcccag tatcagcccg tcatacttga agctaggcag gcttatcttg    11820
gacaagaaga tcgcttggcc tcgcgcgcag atcagttgga agaatttgtt cactacgtga    11880
aaggcgagat caccaaggta gtcggcaaat aatgtctaac aattcgttca agccgacgcc    11940
gcttcgcggc gcggcttaac tcaagcgtta gagagctggg gaagactatg cgcgatctgt    12000
tgaaggtggt tctaagcctc gtacttgcga tggcatcggg gcaggcactt gctgacctgc    12060
caattgtttt agtggatgaa gctcgtcttc cctatgacta ctccccatcc aactacgaca    12120
tttctccaag caactacgac aactccataa gcaattacga caatagtcca tcaaattacg    12180
acaactctga gagcaactac gataatagtt catccaatta cgacaatagt cgcaacggaa    12240
atcgtaggct tatatatagc gcaaatgggt ctcgcacttt cgccggctac tacgtcattg    12300
ccaacaatgg gacaacgaac ttcttttcca catctggcaa aaggatgttc tacacccccaa   12360
aaggggggcg cggcgtctat ggcggcaaag atgggagctt ctgcggggca ttggtcgtca    12420
taaatggcca attttcgctt gccctgacag ataacgccct gaagatcatg tatctaagca    12480
actagcctgc tctctaataa aatgttagga gcttggctgc cattttttggg gtgaggccgt   12540
tcgcggccga gggggcgcagc ccctgggggg atgggaggcc cgcgttagcg ggccgggagg    12600
gttcgagaag gggggggcacc ccccttcggc gtgcgcggtc acgcgcacag ggcgcagccc   12660
tggttaaaaa caaggtttat aaatattggt ttaaaagcag gttaaaagac aggttagcgg    12720
tggccgaaaa acgggcggaa acccttgcaa atgctggatt ttctgcctgt ggacagcccc    12780
tcaaatgtca ataggtgcgc ccctcatctg tcagcactct gccccctcaag tgtcaaggat   12840
cgcgcccctc atctgtcagt agtcgcgccc ctcaagtgtc aataccgcag ggcacttatc    12900
cccaggcttg tccacatcat ctgtgggaaa ctcgcgtaaa atcaggcgtt ttcgccgatt    12960
tgcgaggctg gccagctcca cgtcgccggc cgaaatcgag cctgcccctc atctgtcaac    13020
gccgcgccgg gtgagtcggc ccctcaagtg tcaacgtccg cccctcatct gtcagtgagg    13080
gccaagtttt ccgcgaggta tccacaacgc cggcggccgg ccgcggtgtc tcgcacacgg    13140
cttcgacggc gtttctggcg cgtttgcagg gccatagacg gccgcagcc cagcggcgag     13200
ggcaaccagc ccggtgagcg tcggaaaggg tcgacgatct tgctgcgttc ggatattttc    13260
gtggagttcc cgccacagac ccggattgaa ggcgagatcc agcaactcgc gccagatcat    13320
cctgtgacgg aactttggcg cgtgatgact ggccaggacg tcggccgaaa gagcgacaag    13380
cagatcacgc ttttcgacag cgtcggattt gcgatcgagg attttttcggc gctgcgctac   13440
gtccgcgacc gcgttgaggg atcaagccac agcagcccac tcgaccttct agccgaccca    13500
gacgagccaa gggatctttt tggaatgctg ctccgtcgtc aggctttccg acgtttgggt    13560
ggttgaacag aagtcattat cgcacggaat gccaagcact cccgagggga accctgtggt    13620
tggcatgcac atacaaatgg acgaacggat aaaccttttc acgccctttt aaatatccga    13680
ttattctaat aaacgctctt ttctcttagg tttacccgcc aatatatcct gtcaaacact    13740
gatagtttaa actgaaggcg ggaaacgaca atctgatcat gagcggagaa ttaagggagt    13800
cacgttatga cccccgccga tgacgcggga caagccgttt tacgtttgga actgacagaa    13860
```

-continued

```
ccgcaacgtt gaaggagcca ctcagccgcg gtggcggccg cagtactgag cttcgagaca   13920
agtttgtaca aaaaagcagg ctcatgatta gttagatcaa gcttttgagt cttcaaaaac   13980
ataaaaatta caaaaaaaaa acaaacttaa aatcatttat caatttgaac aacaaagctt   14040
ggccgaatgc taagagctta aaaatggctt cttttgtttc ttttgttgc aaacggtgga    14100 gagaagaggg aaatgaagat tgaccatatt tttttattat gttttaacat ataatattaa   14160
taatttaatc ataattatac tttggtgaat gtgacagtgg ggagatacgt aaagtatata   14220
acattatact ttttgcaagc agttggctgg tctacccaag agtgatcaaa gtttgagctg   14280
ccttcaatga gccaattttt gcccataatg gataaaggca atttgtttag ttcaactgct   14340
cacagaataa tgttaaaatg aaattaaaat aaggtggcct ggtcacacac acaaaaaaaa   14400
actaatgttg gttggttgaa ttttatatta cggaatgtaa tattatattt taaaataaaa   14460
ttatgttatt tagattctta atattttgag cattccatac tataatttcg tatacataat   14520
attaaaatat agtaatataa agtgtaatta actttaaatt acaagcataa tattaaattt   14580
tgaatcaatt aattttttatt tctattattt taattaattt agtctatttt ttcaaaataa   14640
aatttaaatc taaataaaaa taattttttcc ttaatgttga aacaactcat gttatacttc   14700
aaaattataa gtattatatt taccttgatg atttatttat tagtatatta attctgatta   14760
taattatggt gggatacaat cgcttccac taaatatttt aactatgatt tataaattta   14820
tttcaacatc gtatatttac ttattaatac ataatttatc ataattttat ggaaattgag   14880
accaagaaac attaagagaa caaattctat aacaaagaca atttagaaaa aaatgtactt   14940
ttaggtaatt ttaagtactc ttaaccaaac acaaaaattc aaatcaaatg aactaaataa   15000
gataatataa catacggaac atcttacttg taatcttaca ttcccataat tttattatga   15060
aaaataatct tatattactc gaactaaatg ttgtcacaaa ttattatcta aataaagaaa   15120
aacacttaat ttttataaca ttttttcata tatttgaaag attatatttt gtatatttac   15180
gtaaaaatat ttgacataga ttgagcacct tcttaacata atcccaccat aagtcaagta   15240
tgtagatgag aaattggtac aaacaacgtg gggccaaatc ccaccaaacc atctctcatt   15300
ctctcctata aaaggcttgc tacacataga caacaatcca cacacaaata cacgttcttt   15360
tctttctatt tgattaacca cccagctttc                                    15390
```